(12) United States Patent
Pincemail et al.

(10) Patent No.: US 7,288,374 B2
(45) Date of Patent: Oct. 30, 2007

(54) PROCESS FOR THE DETECTION OF OXIDATIVE STRESS AND KIT FOR ITS IMPLEMENTATION

(75) Inventors: Joel Pincemail, Esneux (BE); Jacques Piette, Grivegnee (BE); Daniel Maréchal, Louveigne (BE)

(73) Assignee: Probiox SA, Liege (BE)

( * ) Notice: Subject to any disclaimer, the term of this patent is extended or adjusted under 35 U.S.C. 154(b) by 322 days.

(21) Appl. No.: 10/487,091

(22) PCT Filed: Aug. 13, 2002

(86) PCT No.: PCT/EP02/09079

§ 371 (c)(1),
(2), (4) Date: Jul. 6, 2004

(87) PCT Pub. No.: WO03/016527

PCT Pub. Date: Feb. 27, 2003

(65) Prior Publication Data

US 2005/0112572 A1    May 26, 2005

(30) Foreign Application Priority Data

Aug. 14, 2001 (BE) ................. 2001/0545

(51) Int. Cl.
*C12Q 1/68* (2006.01)
*C07H 21/02* (2006.01)
*C07H 21/04* (2006.01)

(52) U.S. Cl. .......... 435/6; 536/23.1; 536/24.3

(58) Field of Classification Search .......... 435/4, 435/6, 7.1; 536/23.1, 24.3
See application file for complete search history.

(56) References Cited

U.S. PATENT DOCUMENTS

2003/0044878 A1* 3/2003 Leeuwenburgh ............ 435/25
2005/0065446 A1* 3/2005 Talton ..................... 600/529

FOREIGN PATENT DOCUMENTS

| EP | 0 229 674 A2 | 7/1987 |
|----|--------------|--------|
| WO | WO 98/21321 A1 | 5/1998 |
| WO | WO 98/53103 A1 | 11/1998 |
| WO | WO 99/58718 A1 | 11/1999 |
| WO | WO 99/60164 A1 | 11/1999 |
| WO | WO 99/63341 A2 | 12/1999 |
| WO | WO 00/09750 A1 | 2/2000 |
| WO | WO 00/65095 A3 | 11/2000 |
| WO | WO 01/29261 A3 | 4/2001 |
| WO | WO 01/32802 A1 | 5/2001 |
| WO | WO 01/46468 A2 | 6/2001 |

OTHER PUBLICATIONS

Philips et al. Volitile organic compounds in breath as markers of lung cancer : a cross-sectional study. The Lancet 353: 1930-1933 (1999).*
Fiorillo et al., Oxidative stress and Antioxidant Defenses in Renal Patients Receiving Regular Haemodialysis. Clinical Chemistry and Laboratory Medicine 36(3) :149-153 (1998).*
Howard et al. Environmental Tobacco Smoke in the workplace induces Oxidative Stress in Employees, Including increased production of 8-Hydroxy-2'-Deoxyguanosine. Cancer Epidemiology, Biomarkers & Prevention 7 : 141-146 (1998).*
Jain etal., Oxidative Stress in Chronic hepatitis C : not just a feature of late stage disease. J. of Hepatology 36 :805-811 (2002).*
Pascual et al., Hyaluronate levels and markers of oxidative stress in the serum of Sudanese sujects at risk of infection with *Schiistosoma mansoni*. Transactions oif the Royal Society of Tropical Medicine and Hygiene 94 :66-70 (2000).*
Perrin-Nadif et al., Catalase and Supoeroxide Dismutase activities as Biomarkers of Oxidative Stress in workers exposed to Mercury vapors. J. of Toxicology and Environmental Health 48 : 107-119 (1996).*
Kennedy, Christopher H., et al. "Overexpression of hMTH1 mRNA: A Molecular Marker Of Oxidative Stress In Lung Cancer Cells." FEBS Letters. Jun. 5, 1998. pp. 17-20. vol. 29. No. 1. Elsevier Science Publishers, Amsterdam, NL.
Napoli, Claudio, et al. "Multiple Role Of Reactive Oxygen Species In The Arterial Wall." Journal Of Cellular Biochemistry. Jun. 19, 2001. pp. 674-682. vol. 82, No. 4.
Weigel, A. L., et al. Microarray Analysis of Tert-butyl Hydroperoxide and Hydrogen Peroxide Induced Gene Expression In ARPE-19 Cell. Annual Meeting of the Association for Research in Vision and Ophthalmology, Fort Lauderdale, FL. Mar. 15, 2001. p. S754. vol. 42, No. 4.
International Search established for International Patent Application PCT/EP02/009079.
Pincemail, J. et al., "Determination of plasmatic concentrations in antioxidants, antibodies against oxidized LDL, and homocystein in a sampling of Liège population," *Annales de Biologie Clinque*, 58:2 177-85 (2000) (Abstract).

* cited by examiner

*Primary Examiner*—Ethan Whisenant
(74) *Attorney, Agent, or Firm*—Barnes & Thornburg LLP; Sendil K. Devadas

(57) ABSTRACT

The present invention relates to a process for detecting oxidative stress in a sample and to a kit for this implementation. According to one embodiment the present invention provides a method for the detection of oxidative stress in an individual carrying a risk factor for oxidative stress comprising determining the risk factor for oxidative stress of said individual; selecting at least two oxidative stress markers being increased or decreased for said risk factor relative to healthy individuals; and measuring the amount of said at least two oxidative stress markers in a sample obtained from said individual.

41 Claims, 2 Drawing Sheets

PROCESS FOR THE DETECTION OF OXIDATIVE STRESS AND KIT FOR ITS IMPLEMENTATION

This application is the U.S. National Phase of PCT/EP02/09079, filed Aug. 13, 2002, which claims priority to Belgian Application No. 2001/0545, filed Aug. 14, 2001.

The present invention relates to a process for detecting oxidative stress in a blood sample and to a kit for the implementation of this process.

Definition of Oxidative Stress.

Some 98% of the oxygen taken up by our organism is reduced to water at the level of the mitochondrial respiratory chain, in reactions catalyzed by cytochrome oxidase complexes. One molecule of dioxygen yields two molecules of water, by direct capture of four electrons and four protons. Yet oxygen can also undergo stepwise reduction, electron by electron. This leads to formation of highly toxic oxygen species, the activated oxygen species (AOS), the first of which is the superoxide radical anion ($O_2 \cdot ^-$). The chemical structure of the superoxide anion includes an 'unpaired' electron (symbolized by a dot), an essential feature of free radicals. The presence of a free electron makes the radical highly unstable and very reactive as a powerful oxidant. The superoxide anion can in turn capture an electron to become $O^{2-}$ which, in the presence of two protons, will form two new, highly oxidative activated oxygen species: hydrogen peroxide ($H_2O_2$) and single oxygen ($^1O_2$). These two molecules are not free radicals, since all of the electrons in these chemical structures are paired. The electron captured by the superoxide anion can come from another superoxide anion, this leading to spontaneous dis-mutation of the superoxide anion. Coexistence of the superoxide anion with, hydrogen peroxide can yield yet another highly reactive activated oxygen species: the hydroxyl radical OH. This reaction requires the presence of a transition metal such as iron or copper, acting as a catalyst. On the free-radical scene, these metals are key players that cannot be ignored.

By forming AOS, oxygen can aggressively compromise cell integrity. The above-mentioned oxygen species, and particularly free oxygen radicals, have extremely short life spans; they interact with a wide variety of biological substrates such as nucleic acids, nucleotides, proteins, membrane lipids, and lipoproteins. AOS can produce breaks in deoxyribonucleic acid (DNA) and thus alter the genetic message. In the cytoplasm, AOS transform molecules such as NADH or NADPH and thus alter the redox status of the cell and the activity of enzymes using these substrates. The action of AOS markedly modifies the primary, secondary, and tertiary structure of proteins, to the point of denaturing them and forming insoluble aggregates (cell debris). Depolymerization of proteins such as collagen and elastin is a good example of the deleterious action of AOS. The protease inhibitor α-1-antitrypsin (which inhibits elastase and trypsin) is rapidly inactivated by free oxygen radicals. When red blood cells are in contact with AOS for just a few minutes, their hemoglobin is altered; iron is released from the heme, and hemolysis of these cells is increased. Membrane phospholipids are essential constituents of cell architecture. They contain polyunsaturated fatty acids (PUFA), favored targets of free oxygen radicals. The hydrogen located between the double bonds of PUFA is readily pulled off by the hydroxyl radical (OH.), which thus converts the fatty acid (RH) to a free radical (R.). In the presence of oxygen and iron, lipid peroxidation is induced, propagating from fatty acid to fatty acid via formation of free lipid alkoxyl radicals (RO.), peroxyl radicals (ROO.), and lipoperoxides (ROOH). The result is a major alteration of membrane fluidity, possibly leading to cell death. Rich in PUFA, lipoproteins are particularly sensitive to the action of AOS. Oxidized lipoproteins no longer correctly transport cholesterol. In addition, they are recognized by blood macrophages and accumulate inside them. The macrophages then take on the appearance of foam cells, which attach to artery walls. This is the mechanism by which oxidized lipoproteins contribute to increasing the risk of cardiovascular disease.

Recent studies have shown that AOS can also play a role at the molecular level. An example is their action on NF-κB, a B-lymphocyte-specific transcription factor. Maintained inactive in the cytoplasm, NF-κB can be induced in a wide variety of cell types by various factors, including cytokines, infectious agents, and also AOS acting as second messengers. Thioredoxin (TRX), a protein induced by oxidative stress, also increases the activity of NF-κB by modifying the redox regulation of glutathione (GSH). Once activated, NF-κB migrates to the nucleus of the cell, where it can transactivate target genes. It is thus involved in the synthesis of many mediators of the immune and inflammatory responses (cytokines, complement). Several viruses such as HIV also depend on NF-κB to replicate in the cell.

Our organism is always producing AOS but, as will appear in the next section, this production is perfectly regulated by protective systems. AOS thus play an important physiological role, as illustrated in the following examples. Phagocyte cells, neutrophils, eosindphils, and monocytes/macrophages ensure the phagocytosis and destruction of foreign micro-organisms. The cytotoxicity of these cells is due to their ability to shift from a quiescent form to a highly activated form characterized by production of abundant intracellular AOS capable of attacking the membrane of the phagocytosed micro-organism.

Recent studies have shown that in the fertilization process, a spermatozoa secretes large quantities of AOS so as to pierce the membrane wall of the ovum. Under physiological conditions, endothelial cells release a substance called EDRF (endothelium derived relaxing factor), which plays an important role in regulating vascular tonus, because it has muscle-relaxing properties. It has been clearly demonstrated that this EDRF acts like the free nitrogen monoxide NO. radical.

Source of in Vivo AOS Production.

AOS overproduction is attributable to several biochemical mechanisms:

Certainly the most important mechanism is activation of white blood cells by various external stimuli such as endotoxins, interleukins, or complement fragments present in excess in the organism in various pathological situations. The AOS produced via this activation are then secreted into the extracellular medium and can thus attack healthy organs and tissues and trigger acute inflammation. White blood cells also release an enzyme called myeloperoxidase (MPO). In the presence of hydrogen peroxide, this enzyme catalyses oxidation of the chloride ion to a powerful oxidant, hypochloric acid (HOCl), better known as "chlorine bleach".

We have seen that under physiological conditions, mitochondria transform about 2% of their oxygen into AOS. Yet animal studies have shown that this percentage increases during aging, as a result of gradual deregulation of electron transport in the respiratory chain.

Deregulation of electron transport in the mitochondria is also observed in all ischaemia-reperfusion processes. Ischaemia, i.e. oxygen deprivation, in a tissue causes cell lesions in proportion to its duration. To preserve tissue viability, reperfusion must take place within a certain time limit, which depends on the tissue considered. Several experimental and clinical studies have shown, however, that major cell damage occurs when the blood flow-is restored, as a result of explosive production of AOS in the minutes following reperfusion. The conversion of xanthine dehydrogenase (XDH) to xanthine oxidase (XO) (these two enzymes act in the last stages of purine catabolism) is also a major source of AOS. Clinically, ischaemia-reperfusion is an important aspect of stroke and organ transplantation. In cases of oxidative stress, endothelial cells abundantly produce both the superoxide anion and the nitrogen monoxide radical (NO.). Interaction of these radicals has two effects: production of highly toxic peroxynitrites (HOONO) and vasoconstriction due to loss of the vasodilating properties of NO.

AOS, and especially the superoxide anion, can 'activate' iron by releasing it from the storage protein ferritin; the released iron can then initiate free-radical reactions.

Hemoglobin can become a potential oxidant via direct formation of AOS or via. release of heme iron in free form.

In blood platelets, the conversion of arachidonic acid to prostaglandins or leukotrienes, catalyzed respectively by cyclo-oxygenase and lipo-oxygenase, is a potential source of AOS and lipoperoxide production.

Antioxidant Defences.

To protect itself against the potentially harmful effects of oxygen, our organism has developed two types of defense systems.

A primary defense system composed of antioxidant enzymes and compounds. The function of these factors is to prevent the initiation or propagation of free-radical reactions. Enzymatic protection is ensured by superoxide dismutatse (SOD), which destroys the superoxide anion, catalase, which eliminates hydrogen peroxide, glutathione peroxidase, a selenium-dependent enzyme, which converts lipid peroxides to harmless products, iron-chelating proteins (ferritin, transferritin), which maintain in an inactive state iron that would otherwise be capable of catalyzing free radical reactions. In addition, free radicals are destroyed by scavengers, which react directly with the radicals to form oxidized derivatives. For example, glutathione (GSH) reacts with the OH. radical to form oxidized glutathione (GSSG), by a mechanism involving formation of a GS. (thiyl) radical, followed by combination of two such radicals. Other examples of scavengers include uric acid, bilirubin, glucose, thiol proteins (SH proteins), and a group of four vitamins: vitamin A (β-carotene), C (ascorbic acid), E (α-tocopherol), and Q (coenzyme Q-10 or ubiquinone). Remarkably, these antioxidants can act synergistically against free radicals. An example is the cooperation between glutathione and vitamins C and E. When it reacts with a lipid radical R., the lipid is regenerated and vitamin E becomes a tocopheryl radical. Vitamin E is regenerated from this radical through the action of vitamin C, which in turn becomes a radical. This radical then reacts with reduced glutathione, to form vitamin C and a thiyl radical. Two of the latter combine to yield GSSG.

A secondary defense system is composed of proteolytic enzymes. The role of this system is to prevent accumulation of oxidized proteins and DNA in the cell and to degrade their toxic fragments. Phosholipases, DNA endonucleases and ligases, and macroxyproteinases are among the main enzymes forming this last line of defense against AOS.

Pathologies Associated with Increased Oxidative Stress.

Some pathological situations lead to overproduction of AOS. In such situations, an organism's natural defense systems are rapidly overpowered. Generally speaking, oxidative stress is defined as a major imbalance between anti- and pro-oxidants, in favor of the latter, leading to cell damage that is often irreversible.

Overproduction of AOS is considered responsible for about a hundred different pathologies. These fall into 6 major categories: effects due to chemical toxicity (ozone, paraquat) or xenobiotic toxicity, effects due to radiation (γ rays), the hyperoxygenation syndrome (retinopathy of the newborn), inflammatory conditions (rheumatoid arthritis), effects of ischaemia-reperfusion (organ transplantation), degenerative conditions (aging, cancer). Many situations/pathologies are associated with AOS overproduction:

Kidneys: transplantation, glomerular nephritis
Lungs: respiratory distress syndrome, asthma
Heart: coronary thrombosis, transplantation
Skin: burns, sunlight exposure, psoriasis, dermatosis
Brain: trauma, Parkinson's disease, neurotoxins, dementia
Joints: rheumatoid arthritis
Gastrointestinal tract: diabetes, pancreatitis, endotoxemia, intestinal ischaemia
Eyes: cataract, retinopathy (newborn), retinal degeneration
Blood vessels: atherosclerosis
Red blood cells: Fanconi's anemia, malaria
Multiple organs: inflammation, ischaemia-reperfusion, drug toxicity, iron overload, nutritional deficiency (Se), alcohol, radiation, cancer, aging, AIDS.
Liver: Hepatitis C Excessive exercise can also create an oxidative stress in athletes, associated with muscle fatigue and injuries.

When produced in small amounts, AOS trigger an adaptive cell response characterized by increased cell growth, overexpression of antioxidant enzymes (superoxide dismutase), and expression of genes coding for many proteins. Cells exposed to low doses (5 μmoles) of hydrogen peroxide, for example, thus become very resistant to higher concentrations of this oxidant. When produced in excess, AOS attack all the above-mentioned substrates and thus cause often-irreversible cell damage and subsequent tissue necrosis. Between these two extreme situations, there is one where oxidative stress leads to apoptosis, i.e. programmed cell death. This phenomenon involves massive proteolysis and a change in gene transcription, leading to chromatin condensation and DNA fragmentation in the endosomes. Cell integrity is preserved, unlike what happens in pathological necrotic cell death. Before birth, more than one cell out of six dies by apoptosis. Apoptosis is also characterized by major leakage of GSH, rendering the cell more sensitive to oxidative stress.

Antioxidant Therapy.

When oxidative stress largely overwhelms the natural defense systems, recourse to antioxidant therapy is necessary so as to limit the harmful action of AOS. In addition to the natural antioxidants described above, there exist exogenous antioxidants, both natural and synthetic.

Each antioxidant has its specificity. Different ones act at different steps in the AOS production chain. Four major categories can be distinguished:

1. molecules interacting with AOS, either enzymatically (SOD, catalase, glutathione peroxidase) or directly (dimethylsulfoxide, vitamins A, C, and E, ubiquinone, 21-aminosteroids, probucol, captopril, propofol, lipoic acid, flavonoids or P vitamins, . . . );
2. molecules reinforcing the antioxidant defenses of cells. Examples include N-acetylcysteine (NAC), which increases the intracellular GSH concentration, and certain metals acting as cofactors. Copper and/or zinc administration reinforces SOD activity in red blood cells, while selenium reinforces glutathione peroxidase activity in these cells;
3. iron-chelating molecules, one of the best examples being desferioxamine. This compound is notably used to treat idiopathic hemochromatosis. Both the 21-aminosteroids and the flavonoids present in large amounts in *Gingko biloba* possess this interesting iron-chelating capacity;
4. inhibitors of enzymes responsible for free radical formation. The best known is allopurinol, a xanthine oxidase inhibitor used regularly in surgery to limit the effects of ischaemia-reperfusion. Also worth mentioning are certain anti-inflammatory agents (sulfasalasine, 5-aminosalicylic acid) and other products such as ceftazidine and pentoxyfylline, which regulate AOS production by activated white blood cells.

Individuals do not possess identical anti-oxidant potential, as such potential is a function of one's eating habits, lifestyle, genetic characteristics or the environment where one lives. At present, determining an individual's status of oxidafive stress (SSO) has become a priority subject in terms of disease prevention, since numerous studies clearly display a strong link between the alteration of the anti-oxidant defense system and the increased effect of the cardiovascular diseases and cancers.

At the moment, using the development of sensitive and specific techniques which may be used in routine, (on a routine basis 20 assays covering the measure of the anti-oxidants of the trace elements, indicators of stress of the metabolism of iron and of the markers of oxidative stress at the level of the lipids, of the proteins and of the DNA), it is possible to establish a complete blood check-up of the SSO of an individual.

Evidence of in Vivo Oxidative Stress: Classical Assays.

In serum or plasma, the oxidative stress status (SSO) will be estimated in four ways: (i) by measuring antioxidant levels, (ii) by determining trace element levels, (iii) by analyzing the status of iron in the blood, and (iv) by detecting oxidative damage to various biological substrates.

A. Antioxidants.

Vitamin A: Certain carotenoids act as vitamin A precursors, yielding the vitamin through degradation. Vitamin A plays an essential role in visual perception and prevents oxidation of several biological substrates, e.g. the polyunsaturated fatty acids of cell membranes.

Vitamin C: This vitamin reacts with free hydrophilic oxygen-containing radicals. Its plasma level drops very rapidly during oxidative stress. Vitamin C is also involved in regenerating vitamin E. Because vitamin C is very labile, it cannot be assayed correctly unless precautions are taken to preserve the sample (stabilization of the plasma with metaphosphoric acid).

Vitamin E: This term encompasses a group of compounds called tocopherols ($\alpha$, $\beta$, $\gamma$, $\delta$). The most biologically active isomer is $\alpha$-tocopherol, assayed in this study. It reacts with lipid radicals and thus prevents propagation of lipid peroxidation in cell membranes. It acts in close synergy with vitamin C. Its plasma concentration must be standardized with respect to cholesterol.

Reduced glutathione (GSH)/oxidized glutathione (GSSG): The tripeptide glutathione acts at several levels against oxidative stress. It can interact directly with activated oxygen species (AOS), but it is mainly used as a substrate of glutathione peroxidase, which eliminates peroxidised lipids. The GSH/GSSG ratio is one of the most sensitive indicators of oxidative stress in an individual.

Protein thiols (PSH): Most proteins have thiol groups (—SH), which react very-readily with AOS.

Glutathione peroxidase (GPx): Located in red blood cells, GPx requires selenium and reduced glutathione for its antioxidant activity. Its role s to eliminate hydrogen peroxide and lipid peroxides formed when AOS react with polyunsaturated fatty acids.

Superoxide dismutase (SOD): These are metalloproteins of which two varieties are distinguished in man, according to the metal(s) present at the active site. One type contains copper and zinc, while the other requires manganese to be active. The role of these enzymes is to regulate production of the superoxide anion, the first toxic species to be formed from oxygen.

Total plasma antioxidant capacity (analysis of hydrophilic and lipophilic antioxidants): This test evaluates the capacity of plasma to inhibit the production of AOS generated by an in vitro system (the TRAP method). It is thus a screening method that estimates the sum of all individual antioxidant activities present in various biological environments.

B. Trace Elements.

Selenium, Copper, Zinc: These three oligoelements are indispensable to the function of antioxidant enzymes (selenium for GPx, copper and zinc for SOD). Zinc intake leads in the long term to induction of antioxidants such as metallothionines. Zinc also protects the thiol groups of proteins. Zinc can partially inhibit reactions in which copper or iron induces the formation of activated oxygen species. For this reason, the ratio of copper to zinc in the blood may provide interesting information on an individual's level of oxidative stress.

C. Indicators of Oxidative Stress.

Lipid peroxides—oxidized LDL—antibodies against oxidized LDL: Polyunsaturated fatty acids (essential components of cell membranes and lipoproteins) are a preferential target of AOS. These three tests are used to evidence lipid peroxidation. Many studies show a link between, on the one hand, increased LDL oxidation and an increased titre of antibodies against oxidized LDL, and, on the other hand, the appearance of cardiovascular disease, progression of atherosclerosis, and the presence of diabetes.

8-hydroxy-2'-deoxyguanosine (8-OH-dG): AOS react with high affinity with some of the bases that constitute DNA. Guanine is readily transformed to 8-hydroxy-2'-deoxyguanosine (8-OH-dG), which is normally eliminated by DNA repair enzymes. If these systems are deficient, 8-OH-dG accumulates in the DNA, causing mutations implicated in cancer formation. When present in 24-hour urine samples, this marker must be standardized with respect to creatinine.

Carbonyl assay. Oxidative modifications of intracellular proteins have been suggested to play a key role in the causation of senescence-associated losses in physiological functions because oxidized proteins often lose catalytic function and undergo selective degradation. Addition of carbonyl-containing adduct to the side chains of amino-acid residues (lysine, arginine, . . . ) is arguably the most well characterized, age-associated, post-translation structural alteration in proteins.

Myeloperoxidase: When activated, neutrophils increase their oxygen consumption by 400%. This leads to massive production of AOS and to the release of proteolyic enzymes (elastase) and myeloperoxidase (MPO). MPO is involved in the development of oxidative stress, being responsible for the formation of hypochlorous acid, a powerful oxidant. An increased plasma MPO level is thus a specific indicator of neutrophil activation, and this an indirect indicator of the presence of AOS, occurring in all inflammatory processes.

Glucose: By auto-oxidation, glucose yields AOS and glyoxal in large quantities. Glyoxal binds to the amine groups of proteins and hence leads to the appearance of "old proteins" with carboxymethyl-lysine residues. These have the capacity to bind copper and to induce lipid peroxidation, which in turn increases glyoxal production. Glucose itself can bind to hemoglobin to produce glycated hemoglobin. These markers increase, of course, in patients with diabetes, considered a situation of major oxidative stress. Yet aging can also cause these markers to accumulate.

D. Iron Metabolism.

Proteins that bind metal ions: When iron or copper is in a free form, it can catalyze lipid peroxidation and the production of AOS. The capacity of some proteins to bind iron (transferrin, ferritin) or to transport copper (ceruleoplasmin) is an essential preventive antioxidant factor. In the absence of sample hemolysis, an increased saturation of transferritin in iron is an indirect indicator of oxidative stress.

E. Miscellaneous.

Elevated blood levels of homocysteine (a sulfur-containing amino acid) have been linked to increased risk of premature coronary artery disease, stroke, and thromboembolism (venous blood clots), even among people who have normal cholesterol levels. Abnormal homocysteine levels appear to contribute to atherosclerosis in at least three ways: (1) a direct toxic effect that damages the cells lining the inside of the arteries, (2) interference with clotting factors, and (3) oxidation of low-density lipoproteins (LDL).

Detecting an in vivo oxidative stress is thus a long, complex and expensive process which limits its application to medicine, although ways to treat an oxidative stress exist.

Moreover, these diagnostic tests do give a little information on what is going on at the level of the cells, especially at the level of the lymphocytes which metabolism is very dependent on the EOA. Therefore, at the moment no test exists that allows information at this level to be obtained.

One objective of the present invention is to provide a diagnostic test method that allows the status of oxidative stress (SSO) (preferably at the cellular level) to be evaluated quickly and easily.

Furthermore, the invention seeks to provide a kit suitable for performing said method. Further technical problems will be apparent from the subject matter of the claims, the disclosure of which is incorporated hereby.

According to the present invention, the term "risk factor" means any possible physiological and/or pathological condition wherein an individual might be affected by oxidative stress. In particular, intense physical exercise, effects due to chemical toxicity or xenobiotic toxicity, effects due to radiation, hyperoxyegenation syndrome, inflammatory conditions, effects of Ischaemia-reperfusion and degenerative conditions are considered. Below, physiological and/or pathological conditions being characterized by a risk factor for oxidative stress are exemplified.

According to the present invention, the term "anti-oxidant" means any substance capable of protecting from the potentially harmful effects of oxygen; in particular, capable of preventing the initiation of free-radical reactions.

According to the present invention, the term "pro-oxidant" means any substance capable of directly or indirectly supporting the initiation of propagation of free-radical reactions.

According to the present invention, the term "oxidative stress marker" means any marker for oxidative stress known in the art or as described herein.

According to the present invention, the term "protein implied in apoptosis" means any protein being capable of promoting apoptosis, i.e., programmed cell death, or any protein or RNA that is involved in, or regulates, the apoptosis pathway. In particular, molecules being associated with CD95/CD95 ligand (Fas/Fas ligand) are envisaged.

According to the present invention, the term "DNA chip" should be understood as synonymous with microarray or biochip, not being limited to a particular length of nucleic acids or oligonucleotides attached thereto.

According to the present invention, the term "enzyme" also encompasses polypeptides not necessarily exhibiting catalytic activity.

According to the present invention, the term "transcription factors" means any DNA or RNA binding protein or RNA regulating gene transcription and translation, or any RNA, protein, or protein cascade regulating them.

According to the present invention, the term "DNA repair enzyme" means any protein or RNA recognizing DNA modifications or any RNA, protein, or protein cascade regulating them.

According to the present invention, the term "stress protein" means any protein or RNA, expression of which is modified under a cellular stress induced by physical, chemical, or biological conditions outside their normal physiological values.

Surprisingly, the present inventors have discovered that the oxidative stress measured in individuals exposed to different degrees and qualities of oxidative stress differs in its profile of oxidative stress markers, i.e. in the amount of the different oxidative stress markers, when a large variety of stress markers is assessed. For example, the profiles of oxidative stress markers have been obtained from healthy individuals, cardiac patients, hemodialysis patients, people having heavy physical exercise (such as half-marathon athletes and top soccer players.) Although it would have been expected that the amount of oxidative stress markers is increased in the same manner in patients and athletes showing exhaustion due to physical exercise, it has turned out that different oxidative stress markers are selectively induced upon exposure to different sources of oxidative stress; cf. table III. As apparent from tables I and III, some oxidative stress markers are increased under a certain physiological and/or pathological condition, whereas under the same condition different oxidative stress markers may be decreased see e.g. the value for hemodialysis patients from Table III, wherein the average values for lipid peroxide and oxidized LDL are increased, whereas the average values for superoxide dismutase (SOD) and selenium are decreased. These findings have important impacts on the diagnosis and possible therapy of diseases based on oxidative stress.

The present invention allows for the first time a significant reduction in the number of oxidative stress markers to be tested, because only several oxidative stress markers coming from the literature have actually been found to be increased or decreased in individuals having a particular physiological and/or pathological condition when compared to healthy individuals. Additionally, the selection of oxidative stress markers that have been observed to be increased or decreased in a particular physiological and/or pathological condition is reducing the number of false negatives of previous oxidative stress tests that either used markers which are, under the particular physiological and/or pathological condition, neither been increased nor decreased, or included the markers that have been observed to be increased or decreased in a particular physiological and/or pathological condition into a larger panel of non-varying markers, computing an average value that is staying within its normal range. The present invention allows for the risk factor-specific testing of individuals which enables a fine-tuning of diagnosis and possibly also therapy of the underlying oxidative stress syndrome in the physiological and/or pathological condition. Further, the present invention allows for the first time a risk factor-specific evaluation of the data obtained from testing the oxidative stress markers selected according to the present invention which also facilitates the physician to choose a patient-specific treatment regimen.

In one embodiment, the present invention provides a method for determining oxidative stress markers in a group of individuals comprising the steps of:
  a) Determining the risk factor for oxidative stress in said group;
  b) Measuring the amount of at least 10 different oxidative stress markers in a sample obtained from each of said group of individuals; and
  c) Comparing the amount of each of said oxidative stress markers with the amount of each of said oxidative stress markers measured in a group of healthy individuals, thereby determining the oxidative stress markers being increased or decreased in said group of individuals carrying a risk factor for oxidative stress relative to healthy individuals.

The individual may be a human or animal.

The risk factors for oxidative stress are determined by the physician according to general anamnesis. Exemplary risk factors are outlined below.

The measurement of the amount of the oxidative stress markers is determined as outlined below.

Preferably, for statistical reasons, the group comprises at least 10 individuals, preferably more than 50. Subsequent to measurement of the amount of the different oxidative stress markers, the average value is obtained and used for the subsequent comparison step. Also for the group of healthy individuals, at least 10 healthy individuals should be taken in order to obtain reliable average values. Preferably, the group consists of only one gender, (i.e. either male or female), since variations in the amount of oxidative stress markers among men and women have been observed; cf. FIG. 1.

In a further embodiment, the present invention provides a method for the detection of oxidative stress in an individual comprising:
  a) Determining the risk factor of said individual;
  b) Selecting at least 2 oxidative stress markers being increased or decreased for said risk factor relative to healthy individuals;
  c) Measuring the amount of at least 2 of said oxidative markers in a sample obtained from said individual.

Preferably, the oxidative stress markers being increased or decreased for said risk factor are determined by the above method according to the present invention. The sample is preferably a blood sample being obtained by or under the control of a physician.

In a preferred embodiment, said method for the detection of oxidative stress in an individual further comprises the step of evaluating the result in the context of said risk factor without restricting or limiting the physician in any way. It is suggested that the results for a particular oxidative stress marker within a certain individual carrying a risk factor for oxidative stress should be seen in relation to the average value for said oxidative stress marker of the group of individuals carrying the same risk factor for oxidative stress, thereby possibly allowing an estimation of the degree of oxidative stress in said individual carrying the particular risk factor.

The risk factor mentioned in the above methods may be selected from unbalanced diet, smoking habits, exposure to toxic environment, medical surgery, intense physical exercise, and diseases affecting the kidneys, lungs, heart, skin, brain, joints, gastrointestinal tract, eyes, blood vessels, red blood cells, liver and multiple organs.

Preferably, the diseases are selected from transplantation, glomerular nephritis, respiratory distress syndrome, asthma, coronary thrombosis, burns, sunlight exposure, psoriasis, dermatosis, trauma, Parkinson's disease, neurotoxins, dementia, rheumatoid arthritis, diabetes, pancreatitis, endotoxemia, intestinal eschemia, cataracts, retinopathy, retinal degeneration, arteriosclerosis, Fanconi's anemia, malaria, inflammation, ischaemia-reperfusion, drug toxicity, iron overload, nutritional deficiency, alcohol, radiation, cancer, aging, HCV infection and AIDS.

It should be noted that the above list of diseases is non-limited with respect to indications for using the methods according to the present invention. Apart from the above diseases, any physiological and/or pathological situation leading to overproduction of AOS is envisaged by the present invention.

The oxidative stress markers that are useful in the practice of the methods according to the present invention may be selected from the group consisting of antioxidants, trace elements, indicators of oxidative stress, iron metabolism markers, homocysteine, enzymes having antioxidant functions, enzymes having pro-oxidant functions, enzymes for DNA repair, enzymes of the glutathione metabolism, stress proteins, proteins implied in apoptosis, transcription factors, cytokines and chemokines.

Preferably, the antioxidant is selected from vitamin A, vitamin C, vitamin E, reduced glutathione (GSH)Ioxidized glutathione (GSSG), protein thiols, glutathione peroxidase or superoxide dismutase.

Preferably, the trace element is selected from selenium, copper and zinc.

In a preferred embodiment, the indicator of oxidative stress is selected from antibodies against oxidized LDL (low-density lipoproteins), 8-hydroxy-2'-deoxyguanosine, myeloperoxidase, glucose, glyoxal, and oxidized proteins.

Preferably, the iron metabolism marker is selected from transferrin, ferritin, ceruloplasmin.

Preferably, the enzymes having antioxidant function may be selected from catalase, Mn-containing superoxide dismutase (SOD), copper and zinc containing SOD, thioredoxine-1, thioredoxine reductase-1, peroxiredoxin-1, metallothioneine-1, L-ferritine and transferrine receptor, antioxidant protein 2, ceruloplasmin, lactoferrin, selenoprotein P, selenoprotein W, frataxin, serum paraoxonase/arylesterase 1, serum paraoxonase/arylesterase 2, or serum paraoxonase/arylesterase 3.

Preferably, the enzymes having pro-oxidant function may be selected from cyclooxygenase-2,5-lipoxygenase, c-phospholipase A2, phospholipase A alpha, phospholipase D-1, myeloperoxidase, nitric oxide synthetase, C reactive protein, elastase, haptoglobin, NADH-cytochrome b5 reductase or diaphorase A1.

Preferably, the enzyme for DNA repair may be selected from 8-oxoguanine DNA glycosylase.

Preferably, the glutathatione metabolism enzyme may be selected from glutathione peroxidase, non-Se glutathione phospholipid hydroperoxide, phospholipid, gamma-glutamyl cysteine synthetase, and glucose 6-phosphate dehydrogenase, extracellular glutathione peroxidase, glutathione peroxidase, glutathione peroxidase 2, glutathione peroxidase 4, glutathione reductase, glutathione S-transferase, glutathione synthetase, peroxiredoxin 1, peroxiredoxin 2, peroxiredoxin 3, peroxiredoxin 5, or thioredoxin 2.

Preferably, the stress protein may be an HSP protein, heme-oxygenase-1, heme-oxygenase-2, 150 kDa oxygen-regulated protein ORP150, 27 kDa HSP27, HSP90A, HSP17, HSP40 or HSP110.

Preferably, the protein implied in apoptosis may be FasL, CD95, tumor necrosis factor 1, Bcl-2, GADD153, GADD45, RAD50, RAD51B, RAD52, RAD54, p53 or Fas ligand.

Preferably, the transcription factor is selected from NFκB-α, c-Fos, C-jun, IκB-α, monoamine oxidase A, monoamine oxidase B or peroxisome proliferative-activated receptor alpha.

Preferably, the cytokine or chemokine is selected from IL-1, IL-6, IL-8, IL-1 beta, IL-2 or TNF1 receptor associated protein.

The investigations performed by the present inventors have revealed that particular oxidative stress markers are increased or decreased in individuals carrying certain risk factors.

According to a preferred embodiment, the oxidative stress markers being increased or decreased when the risk factor hemodialysis is assessed are catalase, glucose 6 phosphate dehydrogenase, HSP70, 5-lipoxygenase, vitamin C, glutathione peroxidase, SOD, Se, lipid peroxide, oxidized LDL and homocysteine.

The increase or decrease may be either on the transcriptional level and/or on the level of the expressed protein.

According to a further preferred embodiment, the oxidative stress markers being increased or decreased when the risk factor is cardiac surgery are superoxide dismutase containing manganese, c-phospholipase A2, H-ferritin, IL-8, nitric oxide synthase 2 (NOS2), vitamin C, vitamin E/cholesterol, glutathione peroxidase (GPx), antibodies against LDL and homocysteine.

According to a further preferred embodiment, the oxidative stress markers being increased or decreased when the risk factor due to physical exercise is assessed are HSP 70, NFκB-α, vitamin C, copper/zinc ratio, vitamin E/cholesterol, GPx and seric ion.

In athletes carrying the risk factor of heavy physical exercise but also exposed to muscle fatigue and injuries, it has also been observed that the oxidative stress markers being increased or decreased are vitamin E, vitamin E/cholesterol, GSH, GSH/GSSG ratio, zinc, GPx, GSSG, copper/zinc ratio, antibodies against oxidized LDL and oxidized proteins.

According to a further preferred embodiment, the oxidative stress markers being increased or decreased when the risk factor is represented by smoking are vitamin C, Se, GPx, antibodies against oxidized LDL and homocysteine.

According to another preferred embodiment, the oxidative stress markers being increased or decreased when the risk factor is due to a diet lacking fruits are vitamin C, protein thiols, Se, GPx and homocysteine.

According to the present invention when the method for the detection of oxidative stress in an individual is determined as described above, preferably not more than 22 different oxidative stress markers are selected for measuring the amount of the oxidative stress markers in a sample obtained from said individual. Preferably not more than 15, more preferably not more than 10, and particularly preferred not more than 5 different oxidative stress markers being increased or decreased in the group of individuals carrying the particular risk factor of said individuals. As outlined above, the present inventors have recognized that not every single one of the oxidative stress markers known in the art are increased under conditions of oxidative stress in individuals, but that only some depending on the physiological and/or pathological situation, i.e. the risk factor of the individuals are increased. Surprisingly, it has been found that several of the known oxidative stress markers are even decreased in said individuals, whereas oxidative stress markers different than those may be unchanged compared to healthy individuals.

In the methods according to the present invention, the amount of the oxidative stress marker may either be determined by measuring the concentration of the oxidative stress marker or by measuring the concentration of the gene transcript/mRNA or corresponding cDNA encoding the oxidative stress markers.

When the concentration of the oxidative stress marker is determined directly, then any method known in the art for the determination of said oxidative stress marker is encompassed. The determination method may encompass enzymatic, immunochemical or spectroscopic methods. The present invention envisages direct or indirect determination methods such as, for example, radioimmuno assays.

When the amount of the oxidative stress marker is measured by determining the concentration of the gene transcript/mRNA encoding the oxidative stress marker, any method for quantitative determination of gene transcripts known in the art is encompassed hereby. For quantitative determination, it is preferred that the mRNA be converted to the corresponding cDNA by the reverse transcriptase reaction. To determine the corresponding PCR product, quantitative or semi-quantitative PCR methods may be applied. The determination method may also involve hybridization to genes or fragments or derivatives thereof attached to a solid matrix, such as a Northern Blot, for example. The present invention also envisages the use of spectroscopic methods.

It is particularly preferred that the amount of at least 2 of the oxidative stress markers is determined in parallel. The parallel performance of the determination offers the advantage of high-speed determination being recommended in clinical practice.

In regards to this embodiment, it is preferred that the parallel determination of the oxidative stress markers is performed by using a DNA chip (microarray or biochip) as known e.g. van Berkum and Holstege, Biotechniques 2000, 29: 548-560. The chip used for the determination may have any configuration, it is preferred that it allows for duplicate, triplicate, or quadruplicate determinations.

According to another embodiment of the invention, a test kit is provided that is suitable for performing the method for the detection of oxidative stress in an individual. The test kit suitable for performing the method according to the present invention comprises reagents capable of determining the amount of at least 2 oxidative stress markers. Preferably, the reagent capable of determining the amount of said oxidative stress marker is specific to said oxidative stress marker.

According to a preferred embodiment, the reagent capable of determining the amount of said oxidative stress marker is an antibody. The antibody may be monoclonal or polyclonal. Monoclonal antibodies may be obtained by immunizing laboratory animals, removing the splenocytes, and fusing them with tumor cells to obtain oxidative stress marker-specific antibodies by selection according to methods known in the art. Monoclonal antibodies, antibody fragments, or binding molecules may also be selected by using molecular display techniques such as phage display.

The reagent capable of determining the amount of said oxidative stress marker may, in the event that the oxidative stress marker is determined by the concentration of the gene transcript/mRNA or its corresponding cDNA by a probe being essentially complementary to said gene transcript/mRNA or a fragment thereof. It is preferred that the probe comprise at least 10 nucleotides being complementary to the gene transcript/mRNA or fragment thereof. To allow for detection, the probe may also comprise a label being suitable for detection. The label may be radioactive or non-radioactive.

Accordingly, the test kit may comprise an antibody and/or a probe specific to said oxidative stress marker.

According to a preferred embodiment, a process of detecting oxidative stress in a blood sample is provided comprising:
  extracting of mRNA from cells of the blood sample,
  reverse transcribing of said mRNA into cDNA, with labeling of these cDNA compounds,
  bringing these cDNAs into contact with a population of several synthetic DNA fragments, selected in a way to realize a molecular hybridization between the cDNAs and said synthetic DNA fragments, in case of expression of oxidative stress in the cells, and simultaneous detection of signals of said hybridization, which correspond to some expressed genes.

According to a preferred embodiment, the mRNA is extractred from purified lymphocytes.

This process is advantageous for evaluating in one step, by the genetics, the SSO of a patient.

Evidence of In Vivo Oxidative Stress: Innovative DNA Microarray Technology.

An embodiment of this invention is to detect genes expressed during cellular oxidative stress with the plurality of said synthetic DNAs arrayed on a solid support (DNA-arrays). Several solid supports have been described, and methods to prepare and to use the arrays are known (Cheung et al. Nature Genetics Supplement 1999, 21:15-19; Bowtell, Nature Genetics Supplement 1999, 21:25-32; Epstein and Butow, Current Opinion in Biotechnology 2000, 11:36-41; van Berkum and Holstege, Hedge et al., Biotechniques 2000, 29:548-560; Current Opinion in Biotechnology 2001, 12,:48-52, ). Several methods can be used to isolate the RNA from a population of cells, to prepare cDNAs, to post-amplify the cDNAs if needed (low amount of cells), and to label the cDNAs are known (Ausubel et al., Short Protocols in Molecular Biology, Wiley 1999; Wang et al., Nature Biotechnology 2000, 18:457-459; Mansfield et al., Mol Cell Probes 1995, 9:145-56). Several variables need to be controlled for in gene-expression analysis (such as the amount of starting material, enzymatic efficiencies, labeling efficiencies, slide inhomogeneities . . . ) to ensure proper quantitative results. Several calibration methods, using internal (e.g. housekeeping genes like β-actin, cyclophilin, β2-microglobulin, Hypoxanthine phosphoribosyl-transferase I, Ubiquitin C, GAPDH, hydroxymethyl-bilane synthase . . . ) or external ("spiking") controls, are known (Schuchhardt et al., Nucleic Acids Research 1990, 28:e47; Tseng et al., Nucleic Acids Research 1991, 29:2549-2557; Yue et al, Nucleic Acids Research 2001, 29:e41). Image analysis, and data correction and analysis are integrated into several available software tools (Bassett et al., Nature Genetics Supplement 1999, 21:51-55; Quackenbush, Nature Reviews Genetics 2001, 2:418-427).

Preferably, the bringing into presence is realized on a DNA chip which bears said synthetic DNA fragments according to a specific topography.

The process also applies micro array technology.

The high-density DNA chip allows the evaluating of the expression of a great number of genes (for example, the whole genes contained in the organism genome), while the lower-density DNA chip allows the evaluation of the expression of a lower number of genes (often those associated with a pathology). These DNA chips are in technological evolution and they allow the nature and the quantity of some mRNA contained in one cell to be determined in a few hours. The use of these DNA chips has been already considered in a great number of areas in fundamental research but also in applied science, for example, in the follow-up care of cancer patients, people exposed to toxic actions of the environment and in cases of resistance to triple therapy in patients infected by the AIDS virus. These known DNA chips are thus intended for the analysis of a determined pathology.

In the process of the invention, the population of synthetic DNA fragments may be composed of oligonucleotides whose size is between 25 and 100 b, of products from in vitro enzymatic amplification (PCR), or a mixture thereof.

Preferably, the population of synthetic DNA fragments comprises at least 50 gene fragments belonging to the family of genes chosen from the group constituting the enzymes coding for:
  enzymes with antioxidant functions, enzymes with pro-oxidant functions, enzymes for the DNA repair, enzymes of the metabolism of glutathion, stress proteins, proteins implied in apoptosis, transcription factors, cytokines and chemokines.

Preferably, the population of the synthetic DNA fragments selected comprises at least two genes each belonging to one distinct family among the precited families.

More preferably, the population of synthetic DNA fragments comprises one or more fragments of each precited gene families.

As said anti-oxidant enzymes, there may be the following: catalase XM006202, superoxide dismutase containing manganese X14322, superoxide dismutase containing copper and zinc X81859, thioredoxine-1 XM_015718, thioredoxine reductase-1 XM_015673, peroxyredoxine-1 XM_011983, metallothioneine-1 X97261, L-ferritine XM_016853, H-ferritine XM_017556, transferrine receptor XM_002788, antioxidant protein 2 NM_004905, ceruloplasmin M13699, lactoferrin M93150, selenoprotein P Z11793, selenoprotein W U67171, frataxin U43747, serum paraoxonase/arylesterase 3 (PON3) L48516.

As enzymes having pro-oxidant functions, there can be, for example, the following: cyclooxygenase-2 M90100, 5-lipooxygenase XM_005818, c-phospholipase A2 XM_007544, phospholipase A alpha D16234, phospholipase D-1 NM_002662, myeloperoxydase XM_008160, nitric oxide synthetase-2 XM_008631, C reactive protein X56692, elastase M34379, haptoglobin NM_005143, NADH-cytochrome b5 reductase or diaphorase A1 Y09501.

As said enzymes for the DNA repair, there can be, for example, 8-oxoguanine human DNA glycosylase BC000657.

As precited glutathion metabolism enzymes, it can be mentioned for example, the following: glutathione peroxidase X58295, non-Se glutathione phospholipid hydroperoxide AF090194, gamma-glutamyl cysteine synthetase NM_001498, and glucose 6-phosphate dehydrogenase XM_013149, extracellular glutathione peroxidase 2 NM_002083, glutathione peroxidase 4 NM_002085, glutathione reductase X15722, glutathione S-transferase J03746, glutathione synthetase U34683, peroxiredoxin 1 (PRDX1) NM_002574, peroxiredoxin 2 (PRDX2) XM_009063, peroxiredoxin 3 (PRDX3) XM_055573, peroxiredoxin 5 (PRDX5) AF197952, thioredoxin 2 (TRX2) AF276920.

As previously cited stress protein, the following may be mentioned, for example: heat shock protein M11717, heme-oxygenase-1 XM009946, heme oxygenase-2 D21243, 150 kDa oxygen-regulated protein ORP150 U65785, 27-kDa heat shock protein (HSP17) U15590, 40-kDa heat shock protein 1 (HSP40) D49547, 110-kDa heat shock protein (HSP110) D89956, ubiquitin M26880.

As said protein implied in apoptosis, one can mention for example, FasL AF287593, CD95 X89101, receptor 1 tumor necrosis factor M32315, Bcl-2 NM_000633, GADD153 S40706, GADD45 M60974, RAD50 U63139, RAD51B D13804, RAD52 U12134, RAD54 X97795, p53 AF307851, Fas Ligand 38122.

As said transcription factors, the following may be mentioned: IκB-α, c-Fos V01512; C-Jun J04111, IκB-α M69043, monoamine oxidase A (MAOA) M68840, monoamine oxidase B (MAOB) M69177, peroxisome proliferative-activated receptor alpha (PPAR-alpha) L02932.

As said cytokines and chemokines, for example, IL-1 BC-008678, IL-6 BC-015511, IL-8 AF-385628, IL-1β M15330, IL-2 U25676, and TNF1 receptor-associated protein (TRAP1) U12595 can be mentioned.

Said substances are all known and some have received an access number in the PubMed Central and Gene Bank databases, which is cited above.

It must be noted that this list is not all inclusive, but it does permit, during the application of several genes coding for several of these substances, one single analysis of a group of distinct pathologies, each having an effect that may be important, depending on the cases Accordingly, this increases the quality of the analysis and makes it particularly safe, which was not possible until now on the basis of a single known test. In another embodiment of this invention, the expression of the sets of genes identified by DNA array are quantified using quantitative RT-PCR technologies which are more suitable when a limited number of genes (usually less than 10) are to be quantified or when starting with fewer materials (e.g. less than 1 ml blood). Total lymphocyte mRNA is purified as above and the genes are quantified using one or a combination of the RT-PCR technologies, as described by S. A. Bustin (Journal of Molecular Endocrinology, 25, 169-193, 2000) either in separate reactions or in a multiplex format. The design of the amplimers and the probes, of the PCR conditions, and of the RNA controls, and the different labeling options are described by Bustin (ibid.), Graber et al (Current Opinion in Biotechnology 1998, 9:14-18), Schweitzer and Kingsmore (Current Opinion in Biotechnology 2001, 12:21-27) and Lie and Petropoulos (Current Opinion in Biotechnology 1998, 9:43-48). The data are normalized using internal and external controls similarly to what is done with DNA arrays.

Results are reported in absolute concentrations (e.g. average number of mRNA per lymphocyte). Range of normal values in the absence of oxidative stress will be determined as above.

Although described as an independent embodiment, the following subject matter should also be understood as preferred embodiment of the above subject matter. The present invention relates also to a process comprising in addition, before said mRNA extraction, an in vitro exposition of the cells of the blood sample to factors generating oxidative stress, preferably selected from $H_2O_2$, HOCl, xanthine/xanthine oxidase, glucose/glucose oxidase, phorbol myristate acetate, azo-compounds and thermal stress (+41° C.), which allows the evaluation of the efficiency of the selected synthetic DNA fragments before their implementation in a diagnostic test.

The invention also relates to a global evaluation of the SSO by the parallel performance of the single genomic test according to the invention, of the quantification of blood markers of oxidative stress in the sample.

The invention also relates to a kit for the detection of oxidative stress for the implementation of the process characterized in that it comprises:

at least one DNA chip which bears said population of synthetic DNA fragments.

Advantageously, this kit comprises moreover, a hybridization solution adapted to the DNA chip implemented, as well as possibly an adapted washing solution. As a control, it may have at least one gene having a constant expression level in every oxidative stress situation, for example cyclophilline, GAPDH, some beta-actine and ribosomal RNA or an average of several genes. Preferably, this kit presents also a protocol for every necessary step to realize a hybridization and to proceed to the detection of obtained hybridization signals, as well as a reference value table of expressed levels of DNA fragments deposited on said at least one DNA chip, these levels corresponding to a positive value of oxidative stress.

Other methods and forms of realization of the invention are indicated in the claims.

A. EXPERIMENTAL CONDITIONS OF OXIDATIVE STRESS AND EXTRACTION OF mRNA

Figure 1:
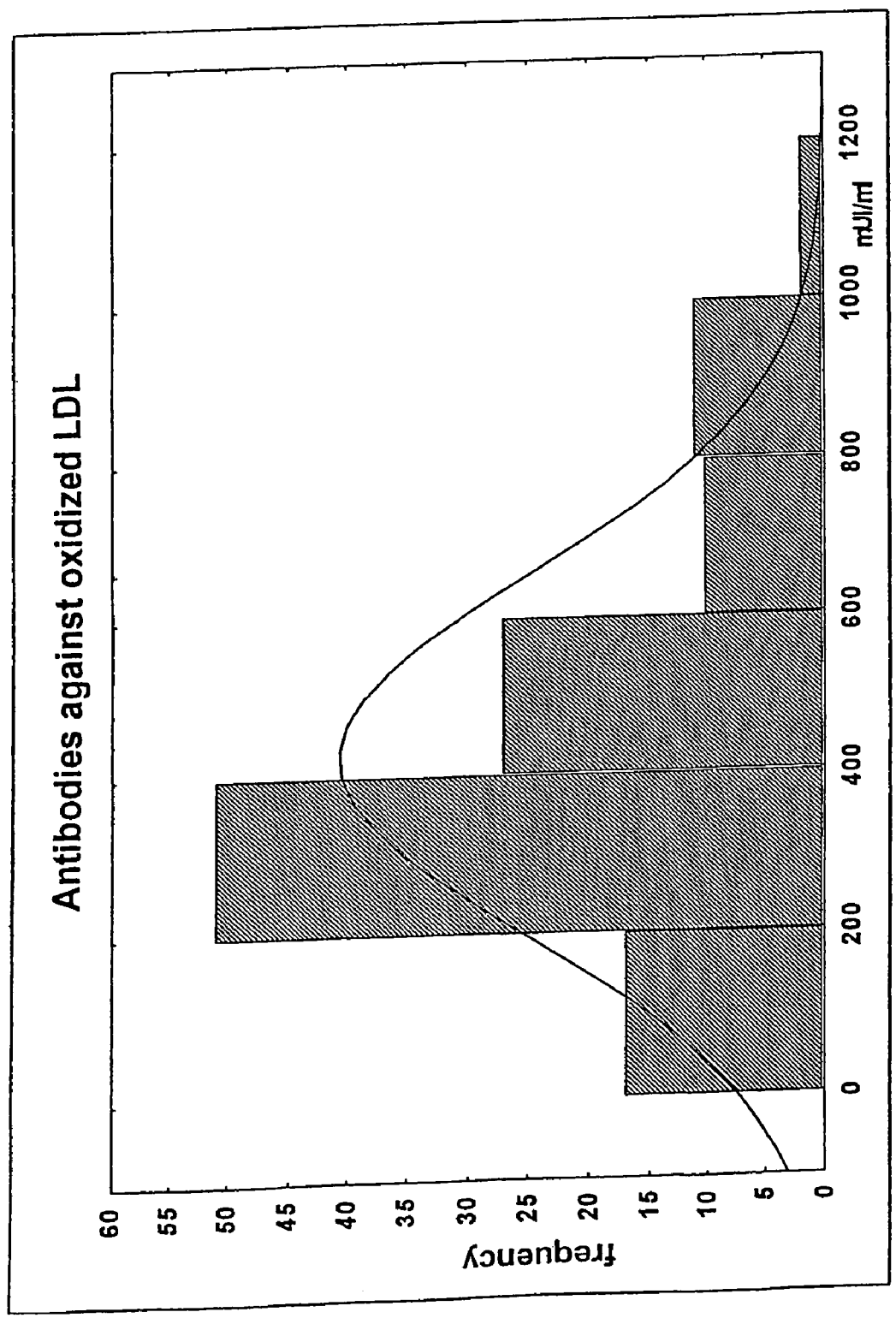
FIG. 1 shows the distribution curve for antibodies against oxidized LDL.

A blood sample (1 ml) taken with heparine as anticoagulant or lymphocytes ($10^7$ cells/ml) isolated from blood samples (coming from the kit from Nycorned Lymphoprep, In VitroGen) are contacted at 37° C. by several production systems of oxidative stress: 1) hydrogen peroxide with a concentration ranging from $10^{-4}$ to $10^{-6}$M; ii) xanthine oxidase 0,4 U/ml/hypoxanthine 2 mM; iii) hydrochlorure 2,2'-azobis(2-amidinipropane) at a concentration of 50 mM. The incubation period may vary between 30 minutes and 3 hours. At the end of the incubation period, the extraction of the RNA messenger is effected from the full blood or from lymphocytes using a commercial kit "μMACS mRNA isolation kit from Miltenyi Biotec Germany".

B. Development of DNA Chips with Low Density SSO

The DNA chips SSO are created simultaneously using PCR products generated by specific oligonucleotides from genes sequences candidates chosen for example, between those detailed above, as well as from polynucleotides representing fragments of these genes. The size of the PCR products will be in this example comprised between 400-600 pairs of bases and the size of polynucleotides will be between 60-80 bases. The system used for the deposition of the products on the glass blade is EuroGridder SDDC-2.

C. Preparation of Fluorescent Probes (Complementary DNA) and Hybridization of the DNA Chips SSO The RNA messengers extracted are transformed into complementary DNA by reverse transcription. The reverse transcriptase is the SuperScript II sold by Invitrogen/Life Technology. The protocol of the reverse transcription is the one coming with the enzyme. The complementary DNA are then amplified by PCR using the specific oligonucleotides of the selected genes and the polymerase SilverStar (Eurogentec) according to the protocol given with the enzyme. The labeling is done during the amplification by incorporation of dCTP coupled with either CY3 or either CY5 (from Amersham/Pharmacia). The complementary DNA are then put together and diluted in a hybridization solution "Dig Easy Hybridization solution" sold by Roche Boehringer and deposited on the DNA chips (20 µl per blade, covered by a cover slip of 24×32 mm). The blades are then put individually in hybridization rooms sold by Corning and incubated during 5 to 16 hours at 42° C.

D. Washing of the DNA Chips, Detection and Analysis of the Hybridization Signals After hybridization, the DNA chips are washed twice for 5 minutes successively in solutions 0.2×SSC-0.1% SDS and 0.2×SSC a (1×SSC=0,15 M NaCl–0,015 M citrate sodium, pH: 7,5). The hybridization signals are measured with the scanner GenePix 4000A and the results are treated with the GenePix software 3.0 from Axon Instruments.

E. Validation of the Tests on DNA Chips of Low Density SSO

For each tested gene, reference values are established from a range of samples obtained from 50 patients in good health. The quantification of the gene expression will be done compared to the basic expression of genes like cyclophilline, GAPDH, the beta-actine and the ribosomal RNA. These values are compared to the ones obtained on the blood samples submitted to in vitro oxidative stress as described above.

The efficiency of DNA chips SSO is also preferably being tested on patients having an oxidative stress which has been evidenced and this on the basis of classical blood dosage.

Once the efficiency of the DNA chips is observed, these can be directly applied to diagnose an oxidative stress situation on patients who may possibly suffer from such a situation.

Material and Methods

A. Detection of Oxidative Stress.

A battery of 22 assays is used to evidence in vivo oxidative stress. They include the determination of antioxidant and trace elements, the analysis of oxidative damage to lipids and proteins, and the investigation of iron metabolism. The normal range for each assay was established on a population of 123 healthy and sedentary individuals (age 21-64 years). Blood samples were drawn on appropriated anticoagulant and immediately spun. Plasma aliquots were kept at −20° C. until assay.

Antioxidants.

Because it is highly labile, plasma vitamin C or ascorbic acid was estimated spectrophotometrically using reduction of the dye 2,6-dichlorophenolindophenol (Merck, Germany) after stabilization with a 10% metaphosphoric acid solution as previously described (Omaye S et al., Methods Enzymol. 62: 3-11; 1979).

Plasma vitamin E or α-tocopherol concentration was assessed by high-pressure liquid chromatography (HPLC) on reversed phase column C-18 120 (100×4.5 mm i.d.) with an isocratic elution with methanol/water (98:2) and ultraviolet radiation (UV) detection at 280 nm, according to Bieri et al. (Am. J. Clin. Nutr. 32: 2143-2149; 1979). As vitamin E is carried by lipids, vitamin E status was expressed as vitamin E/cholesterol ratio.

Plasma vitamin A concentration was analyzed by HPLC and UV detection at 325 nm using kit provided by Chromsystems (Munich, Germany).

Reduced (GSH) and oxidized (GSSG) glutathione were assessed by the calorimetric determination using the thiol-scavenging reagent, 1-methyl-2-vinylpyridinium trifluoromethanesulfonate (Bioxytech GSH/GSSG-412, Oxis, USA).

Proteins sulfhydryl (P-SH) groups concentration was assessed in plasma by the spectrophotometric method using 5,5'-dithio-bis (2-nitrobenzoic acid) (Sigma, Steinheim, Germany) reduction according to Ellman et al. (Arch. Biophys. 82: 70-77; 1959).

Glutathione peroxidase (GPx) and superoxide dismutase (SOD) enzymes were assessed in the whole blood using a spectrophotometric method adapted to routine assay (Randox Laboratories, Antrim, UK).

Trace Elements.

Selenium, copper and zinc were measured on plasma by a direct graphite-furnace atomic-absorption-spectroscopic procedure on a SP IRAA-640 (Varian, the Netherlands) equipped with a Zeeman background correction (Nève J. et al., in: Bratter P; Schamer P., eds. *Trace elements analytical chemistry in medicine and biology*. Berlin: Walter de Gruyter; 1987: 1-10). The ratio copper/zinc was used as a sensitive marker of the presence of in vivo oxidative stress (Mezzetti A. et al., Free Rad. Biol. Med., 25; 676-681; 1998).

Markers of Oxidative Stress.

The concentration of lipid peroxide was determined by reaction of the biological peroxides with peroxidase and a subsequent color-reaction using TMB as substrate. After addition of a stop solution, the colored liquid was measured photometrically at 450 nm.

Oxidized LDL was determined by an Elisa technique developed by Mercodia (Uppsala, Sweden). It was based on the direct sandwich technique in which two monoclonal antibodies are directed against separate antigenic determinants on the oxidized apolipoprotein B molecule.

Autoantibodies against oxidized LDL (ox-LDL-Ab) were determined with a commercially available enzyme immunoassay (Biomedica Gruppe, Vienna, Austria) initially developed by Tatzber and Esterbauer (in: Rice-Evans, C.;

Bellomo, G. eds. *Free radicals IX*. London: Richelieu Press; 1995: 245-262). Copper ($Cu^{2+}$) oxidized LDL was coated onto microtiter strips as antigen. Autoantibodies, if present in the prediluted plasma, bound specifically to the antigen. After a washing step, a specific peroxidase conjugated antihuman IgG antibody detected the presence of bound autoantibodies. After removal of unbound conjugate through washing, tetramethylbenzidine was added to wells as a nontoxic chromogenic substrate. The concentration of specific IgG in the sample was quantitated by an enzyme catalyzed color change detectable on a standard ELISA reader.

The degree of protein oxidation was monitored by the method of Levine et al. (Methods Enzymol. 186: 464-478; 1990), which uses the reaction of 2,4-dinitrophenylhydrazine (DNPH) with the carbonyl groups of oxidized proteins. Protein carbonyls were then read at 370 nm and evaluated using a molar absorption coefficient of $22,000$ $M^{-1}cm^{-1}$.

F. Iron Metabolism

Seric iron was determined after reduction of ferric ions into ferrous ions which react with ferrozine reagent to form a red colored complex. Absorbency was read at 572 and 660 nm (kit Merck n° 19725).

The ADVIA Centaur Ferritine measure is a two sites immunodosage (sandwich), using a direct chemiluminescence technology and constant quantity of anti-ferritine antibodies. The first antibody is an anti-ferritine goat polyclonal antibody, coupled with acridinium ester. The second antibody is an anti-ferritine mouse monoclonal antibody covalently bounded to paramagnetic particles.

Transferrin was analyzed by immunoturbidimetric test using kit from Aptec, catalog n° 53-080040/1.

G. Miscellaneous

Total homocysteine (tHcy) (µmol/L) was measured by HPLC coupled with fluorescence detection as described by Jacob et al. (Ann. Biol. Clin. (Paris), 55: 583-591; 1997).

H. Establishment of Reference Values

When the parameter observed shows a good normal distribution in the population studied, its reference value is defined as the mean±twice the standard deviation (SD) obtained from the absolute frequency histogram after defining appropriate classes (Gaussian distribution optimized by successive iterations). Differences between mean concentrations recorded for different sub-groups (smokers, fruit eaters . . . ) were evaluated by means of Student's t-test for independent variables. Differences were judged statistically significant at $p < 0.05$. Correlations were calculated by multiple regression of the various independent variables.

B. Microarray Experimentation.

The use of DNA arrays (cDNA microarrays or oligonucleotide microarrays) has been proposed a powerful technology to assess antioxidant and prooxidant gene expression. Blood samples obtained at rest from 16 healthy adults were collected as control population. With regard to the classical blood analysis, no significant oxidative stress was detected in this population (a maximum of 2 abnormal parameters on 6 investigated assays as shown on table I).

We started an experimental design to analyze the expression profiles of lymphocytes in three in vivo conditions of oxidative stress:

A. Patient with chronic renal failure; blood samples were collected before hemodialysis. This test sample was compared to gene expression profile found in the control population.

B. Patient submitted to cardiac surgery associated with cardio-pulmonary bypass procedure; blood samples were collected before (reference cDNA in the present situation) and 24 h after cardiac surgery (test sample).

C. Six well-trained athletes (five male and one female) performed an official half-marathon; blood samples were collected at rest (reference cDNA in the present situation) and within 1 hour after the competition (test sample).

The preparation of lymphocytes was started within 1 hour after blood collection.

Microarray Preparation

Preparation of the cDNAs: Primary polymerase chain reaction (PCR) were realized: 10 µl mix of specific primers 1 and 2 (vol. 1:1; cf. table IIa) and 90 µl PCR mixture containing 20 ng human cDNA pool, 10× EuroTaq DNA polymerase buffer, 2 mM $MgCl_2$, 0.8 mM dNTP and 0.02 U/µl EuroTaq DNA polymerase (Eurogentec, Belgium). Amplification was then performed with denaturation for 5 min at 94° C., followed by 40 cycles of denaturation at 94° C. for 1 min, annealing at 55° C. for 30 sec and extension at 72° C. for 1 min.

Amino-modified PCR were realized with 30 µl primary PCR products and 70 µl PCR mixture containing 10× EuroTaq DNA polymerase buffer, 2 mM $MgCl_2$, 0.8 mM dNTP and 0.02 U/µl EuroTaq DNA polymerase (Eurogentec, Belgium) added by 20 pmol of reverse primer: 5'-GTC-CGG-GAG-CCA-TG-3' (seq75) and 20 pmol of forward primer: 5'-CGA-CGC-CCG-CTG-ATA-3' (seq76). Amplification was then performed with denaturation for 5 min at 94° C., followed by 40 cycles of denaturation at 94° C. for 1 min, annealing at 45° C. for 30 sec and extension at 72° C. for 1 min.

Purified amino-modified PCR products and long oligos (~65 mer; at a concentration of 10 µM; cf table IIb), were arrayed onto Diaglass microscope slides (Advanced Array technology, Namur, Belgium) using Eurogridder SDDC-2 robotics (ESI/Virtek).

A total of 32 cDNAs and 10 long oligos were arrayed in 1 $cm^2$ areas (Tables IIa and IIb). Printed arrays were washed once with 0.2% SDS for 2 min, twice with distilled water for 2 min, and incubated once for 5 min in sodium borohydride solution ($NaBH_4$ 2.5 mg/ml dissolved in a PBS/EtOH solution (75/25)). The arrays were washed once with distilled water for 2 min and submerged in distilled water heated to 95° C. for 3 min, air dried and then stored in the dark at room temperature.

Preparation of Leukocytes for cDNA Hybridization

EDTA blood was first diluted in PBS Dulbecco's (Gibco,) (1:1). Ten milliliters of EDTA blood-PBS were carefully layered over 5 ml of Lymphoprep (Axis-Shield, Oslo, Norway) and centrifuge for 20 min at 3000 rpm. The erythrocytes were sedimented to the bottom of the tube. The majority of the leukocytes remained in the plasma layer and were removed. The overlay was washed two times with PBS, and the leukocytes were counted in a Cell-Dyn 1600 (Sequoia-Turner).

Isolation of RNA and cDNA Array Hybridization

Total RNA were isolated from lymphocytes using Rneasy kit (Qiagen, Germany), as described by the manufacturers. Final concentrations were monitored by spectrophotometry. Reverse transcriptions (RT) were performed with 1 µg total RNA, first strand buffer 5×, 0.1 pmol/µl "Specific Primer Mix" (10 µl of all primers 1 and primers 2 added by 290 µl Rnase free water), 1.5 mM dNTP (w/o dCTP), 0.025 mM dCTP, 1.25 nM biotin-labeled and fluorescent-labeled dCTP (PerkinElmer-life sciences, USA), 0.01 M DTT, 1.5 µg oligo dT, 3 µg anchored oligo dT, 1 µl Superscript II Rnase H-Reverse Transcriptase enzyme (Invitrogen, USA) and 1 µl Rnase OUT (Invitrogen, USA). Biotin and fluorescent-labeled cDNA were pooled, purified and concentrated with microcon-YM30 filter (Millipore, Mass., USA). The labeled probes were then resuspended in 20 µl hybridization buffer (5×SSC, 2% SDS, 20% Formamide) added by 0.5 µl DNA salmon sperm and was applied slowly under the cover-slip of the DNA microarray. Hybridization was carried out overnight at 42° C. inside a hybridization chamber (Corning, N.Y., USA).

Posthybridization and Cyanine-3 (Cy3™) and Cyanine-5 (Cy5™) TSA

After hybridization, the microarray was washed with 30 ml 0.5×SSC, 0.01% SDS, and then with 30 ml 0.06×SSC, 0.01% SDS. Finally, the microarray was washed with 0.06× SSC. The signal is amplified by the tyramide signal amplification (TSA) system MICROMAX (Perkin Elmer-life sciences, USA) as described by the manufacturer. Briefly, hybridization signal from biotin-labeled cDNA was amplified with streptavidin-horseradish peroxidase (HRP) and Cy5-tyramide, while hybridization signal from fluorescent-labeled cDNA was amplified with anti-fluorescent-HRP and Cy3-tyramide. After signal amplification and posthybridization wash, the DNA microarray was air-dried and detected with a laser scanner.

Image Acquisition and Data Analysis

Laser detection of the Cy3 and Cy5 signal on the microarray was acquired with a GenePix 4000A (Axon Instruments; CA, USA). The fluorescence signal intensities and the Cy3/Cy5 ratios were analyzed by the software GenePix Pro 3.0 (Axon Instruments; CA, USA).

The background-substracted intensities of all cDNA and oligo hybridizations were normalized to each other by the ratios of total Cy3 and Cy5-fluorescence values. Three housekeeping genes (cyclophilin, β-actin and GAPDH) have been used as internal controls. Thus, hybridization signals from these control genes in two RNA samples should theoretically be the same. The Cy3-to-Cy5 ratios for each of these control genes must be closed to 1.

TABLE I

OXIDATIVE STRESS LEVEL IN BLOOD SAMPLE OF A CONTROL POPULATION FROM WHICH LYMPHOCYTES HAVE BEEN ISOLATED FOR DNA MICROARRAY ASSAY.

| Sex | age | no smoker/ smoker | Vit.C (µg/ml) | LDL Ox (U/l) | αLDLox (mIU/ml) | Lipid peroxides (µmol/l) | GSH (µmol/l) | GSSG (µmol/l) | Ratio GSH/ GSSG |
|---|---|---|---|---|---|---|---|---|---|
| F | 22 | S | 12.9 | 57.61 | X | 867.8 | 879.55 | 2.11 | 414.99 |
| M | 34 | NS | 10.8 | 59.64 | 595.17 | 356.78 | 602.15 | 0.25 | 2406.62 |
| M | 27 | S | 5.58 | 81.53 | 119.47 | 313.55 | 899.68 | 5.94 | 149.4 |
| F | 35 | NS | 13.6 | 49.04 | 138.27 | 245.96 | 817.23 | 2.75 | 294.98 |
| F | 26 | S | 9.15 | 91.27 | 167.42 | 715.98 | 803.17 | | |
| M | 47 | NS | 6.1 | 107.9 | 224.76 | 196.97 | 845.67 | 0.18 | 4610.77 |
| M | 53 | NS | 9.18 | 64.93 | 135.45 | 168.33 | 753 | | |
| M | 34 | NS | 9.23 | 61.27 | 265.19 | 136.87 | 973.51 | 0.65 | 1499.98 |
| F | 42 | NS | 14.3 | 63.1 | 195.62 | 227.54 | 804.77 | 1.66 | 482.48 |
| M | 51 | NS | 13.6 | 64.12 | 142.03 | 219.21 | 906.4 | 0.16 | 5824.83 |
| M | 39 | NS | 6.6 | 56.06 | 354.5 | 108.74 | 728.07 | 1.46 | 497.56 |
| F | 36 | NS | 21.6 | 33.93 | 419.36 | 169.88 | 874.12 | 0.71 | 1224.04 |
| M | 24 | NS | 12.3 | 60.45 | 491.75 | 138.61 | 877.63 | 0.82 | 1062.99 |
| F | 23 | NS | 1.75 | 66.8 | 162.72 | 629.48 | 754.27 | 0.87 | 866.46 |
| M | 39 | NS | 7.51 | 73.07 | 1434.7 | 267.5 | 982.46 | 28.15 | 32.9 |
| M | 32 | S | 8.04 | 147.1 | 482.35 | 72.259 | 866.45 | 1.41 | 612.82 |
| Mean | 35 | | 10.14 | 71.11 | 355.25 | 302.22 | 835.51 | 3.37 | 1427.20 |
| S.D. | 9.6 | | 4.61 | 26.38 | 336.06 | 232.24 | 95.84 | 7.29 | 1737.16 |
| Normal range N = 123 | | | 4-10 | 26-117 | 200-600 | <400 | 753-958 | 1.17-5.32 | 156-705 |

TABLE IIA

Sequences of human genes selected primers used to detect oxidative stress.

| GENES | ACCESS N° | PRIMER 1 | PRIMER 2 |
|---|---|---|---|
| Catalase | XM_006202 | GATATGGATCACATACTTTCAAGCTGG (SEQ ID NO: 1) | GGTAGGGACAGTTCACAGGTATATG (SEQ ID NO: 2) |
| Mn superoxide dismutase | X14322 | GTGGTGGTCATATCAATCATAGCATT (SEQ ID NO: 3) | CATTCCAAATAGCTTTTAGATAATCAG (SEQ ID NO: 4) |
| Cu/Zn superoxide dismutase | X81859 | GCAATGTGACTGCTGACAAAGAT (SEQ ID NO: 5) | ATGATGCAATGGTCTCCTGAGAG (SEQ ID NO: 6) |
| Thioredaxin 1 | XM_015718 | TTGTAGTAGTTGACTTCTCAGCC (SEQ ID NO: 7) | CCACCTTTTGTCCCTTCTTAAAA (SEQ ID NO: 8) |
| Thioredoxin reductase-1 | XM_015673 | CCTATGACTATGACCTTATCATCATTGG (SEQ ID NO: 9) | CCTTAATCCTGTGAGGACCAATAAA (SEQ ID NO: 10) |

TABLE IIA-continued

Sequences of human genes selected primers used to detect oxidative stress.

| GENES | ACCESS N° | PRIMER 1 | PRIMER 2 |
|---|---|---|---|
| Peroxiredoxin-1 | XM_011983 | TTCTTTCAGATTTGACCCATCAGATC (SEQ ID NO: 11) | GGGATTATCTGTTTCACTACCAGGT (SEQ ID NO: 12) |
| L-ferritin | XM_016853 | CCAGATTCGTCAGAATTATTCCAC (SEQ ID NO: 13) | TAAGCTTCACTTCCTCATCTAGG (SEQ ID NO: 14) |
| H-ferritin | XM_017556 | TCTTCACCAATCTCATGAGGAGAGG (SEQ ID NO: 15) | TGGTCACATGGTCATCCAATTCTT (SEQ ID NO: 16) |
| Transferrin receptor | XM_002788 | TTTATACACTCCTGTGAATGGATCTATAG (SEQ ID NO: 17) | CAACATAGTGATCTGGTTCTACAAAG (SEQ ID NO: 18) |
| Pro-oxidant enzymes: | | | |
| Cyclo-oxygenase-2 | M90100 | CAGAAATACAACTATCAACAGTTTATCTAC (SEQ ID NO: 19) | GTAGGCAGGAGAACATATAACATTA (SEQ ID NO: 20) |
| 5-lipoxygenase | XM_005818 | TGATATCCAGTTTGATAGTGAAAAAGG (SEQ ID NO: 21) | GAAGGGAGGAAAATAGGGTTCTC (SEQ ID NO: 22) |
| Phospholipase A2 | XM_007544 | CTCATCCTGTCATTGGACTACAACC (SEQ ID NO: 23) | GGTTGTTGCAGACATTGTAATGTG (SEQ ID NO: 24) |
| Phospholipase A alpha | D16234 | CATTAGTGATAAAGATGCCTCTATAGTAG (SEQ ID NO: 25) | CACATCATAGTAAGCAATAAGTAAGTC (SEQ ID NO: 26) |
| Phospholipase D1 | NM_002662 | CTGACATGAGTAATATCATAGAAAATCTGG (SEQ ID NO: 27) | CCATGTGTTAATTCAATAGTGTAAAGATT (SEQ ID NO: 28) |
| Myeloperoxidase | XM_008160 | GTTCCTACAATGACTCAGTGGACC (SEQ ID NO: 29) | CATACTGCTCCATCAGTTTCCTC (SEQ ID NO: 30) |
| Nitric oxide synthase-2A | XM-008631 | CTTCATGAAGTACATGCAGAATGAATAC (SEQ ID NO: 31) | CCTGTACTTATCCATGCAGACAAC (SEQ ID NO: 32) |
| Enzymes for the DNA repair: | | | |
| 8-oxoguanine DNA glycosylase | BC000657 | CAAGTATGGACACTGACTCAGACTG (SEQ ID NO: 33) | ATGTGCCACATATGGACATCCAC (SEQ ID NO: 34) |
| Enzymes for glutathione metabolism: | | | |
| Glutathione peroxidase | X58295 | GACAAGAGAAGTCGAAGATGGAC (SEQ ID NO: 35) | TCTTCCTGTAGTGCATTCAGTTC (SEQ ID NO: 36) |
| Non-Se glutathione phospholipid hydroperoxide | AF090194 | AGACTCATGGGGCATTCTCTTCT (SEQ ID NO: 37) | CAGGACCAAAAATAAACACCACAC (SEQ ID NO: 38) |
| γ-glutamylcysteine synthetase | NM_001498 | CATTTATAGAAACATTTACTGAGGATGATG (SEQ ID NO: 39) | TGTCTATTGAGTCATATCGGGATTT (SEQ ID NO: 40) |
| Glucose-6-P dehydrogenase | XM_013149 | TCTATGTGGAGAATGAGAGGTGGG (SEQ ID NO: 41) | ATAAATATAGGGGATGGGCTTGG (SEQ ID NO: 42) |
| Stress proteins: | | | |
| Heat shock protein-70 | M11717 | CCATGGTGCTGACCAAGATGAAG (SEQ ID NO: 42) | GCTGATGTCCTTCTTGTGTTTTC (SEQ ID NO: 43) |
| Heat shock protein 70 | M15432 | CCATGACGAAAGACAACAATCTG (SEQ ID NO: 44) | AGATGACCTCTTGACACTTGTCC (SEQ ID NO: 45) |
| Herne Oxygenase-1 | XM_009946 | CAGGCAGAGGGTGATAGAAGAGG (SEQ ID NO: 46) | GAGTGTAAGGACCCATCGGAGAA (SEQ ID NO: 47) |
| Transcription factors: | | | |
| 1κB-α | M69043 | TCTACACTTAGCCTCTATCCATGG (SEQ ID NO: 49) | TGAAGGTTTTCTAGTGTCAGCTG (SEQ ID NO: 50) |
| c-Fos | V01512 | GAGACAGACCAACTAGAAGATGAGA (SEQ ID NO: 51) | ATAGAAGGACCCAGATAGGTCCA (SEQ ID NO: 52) |

TABLE IIA-continued

Sequences of human genes selected primers used to detect oxidative stress.

| GENES | ACCESS N° | PRIMER 1 | PRIMER 2 |
|---|---|---|---|
| Cytokines: | | | |
| Interleukin-8 | AF385628 | ATAAAGACATACTCCAAACCTTTCC (SEQ ID NO: 53) | GGTCCACTCTCAATCACTCTCAG (SEQ ID NO: 54) |
| Interleukin-6 | BC015511 | TTTAAATATGTGAAGCTGAGTTAATTTATG (SEQ ID NO: 55) | AATGCCATTTATTGGTATAAAAACC (SEQ ID NO: 56) |
| Interleukin-1 | BC008678 | GAGAAGAAAGTAATGACAAAATACCTG (SEQ ID NO: 57) | AAATTGCATGGTGAAGTCAGTTATA (SEQ ID NO: 58) |
| House keeping genes: | | | |
| Cyclophilin | | GTCCGGGAGCCATGCCGTGTTCTTCGACATT (SEQ ID NO: 59) | CGACGCCCGCTGATATGGCCTCCACAATATT (SEQ ID NO: 60) |
| β-actin | | CTCTTCCAGCCTTCCTTCCT (SEQ ID NO: 61) | CACCTTCACCGTTCCAGTTT (SEQ ID NO: 62) |
| GAPDH | | CGAGATCCCTCCAAAATCAA (SEQ ID NO: 63) | TGAGCTTGACAAAGTGGTCG (SEQ ID NO: 64) |

TABLE IIb

Sequences of human genes selected long oligos used to detect oxidative stress.

| GENES | ACCESS N° | LONG OLIGO |
|---|---|---|
| Anti-oxidant enzymes: | | |
| Catalase | XM_006202 | GAGCCTGGATGTGGCTCCCGTAGTCAGGGTGGACCTCAGTGAAGTTCTTGACCGCTTTCTTCTGG (SEQ ID NO: 65) |
| Mn superoxide dismutase | X14322 | GCTGTAACATCTCCCTTTGCCAACGCCTCCTGGTACTTCTCCTCGGTGACGTTCAGGTTGTTCAC (SEQ ID NO: 66) |
| Thioredoxin 1 | XM_015718 | GGCCCACACCACGTGGCTGAGAAGTCAACTACTACAAGTTTATCACCTGCAGCGTCCAAGGC (SEQ ID NO: 67) |
| Thioredoxin reductase-1 | XM_015673 | CCAGCAAGAAATCCAGCGCACTCCAAAGCGACATAGGATGCTCCAACAACCAGGGTCTTACCCGG (SEQ ID NO: 68) |
| Peroxiredoxin-1 | XM_011983 | AGCTGTTCCTTCCCAGTAGGGCGCTGGCTTGGAAATCTTCGCTTTGCTTAGGTGCAGGGAGTG (SEQ ID NO: 69) |
| Enzymes for glutathione metabolism: | | |
| Glutathione peroxidase | X58295 | CAAAGTTCCAGCGGATGTCGTGAACCTTCATGGGTTCCCAGAAGAGGCGGTCAGATGTACCCAGG (SEQ ID NO: 70) |
| Non-Se glutathione phospholipid hydroperoxide | AF090194 | GGCTGGGGTGTGTAGCGGAGGTATTTCTTGCCAGATGGGAGCTCTTTGGTGAAGACTCCTTTAGG (SEQ ID NO: 71) |
| γ-glutamylcysteine synthetase | NM_001498 | CCTTCCGGCGTTTTCGCATGTTGGCCTCAACTGTATTGAACTCGGACATTGTTCCTCCGTAGGGC (SEQ ID NO: 72) |
| Glucose-6-P dehydrogenase | XM_013149 | AGGATGAAGGGCACCCCATCCCACCTCTCATTCTCCACATAGAGGACGACGGCTGCAAAAGTGGC (SEQ ID NO: 73) |

TABLE IIb-continued

Sequences of human genes selected long oligos used to detect oxidative stress.

| GENES | ACCESS N° | LONG OLIGO |
|---|---|---|
| Stress proteins: | | |
| Heme oxygenase-1 | XM_009946 | GGCATAAAGCCCTACAGCAACTGTCGCCACCAGAAAGCTGAGTGTAAGGACCCATCGGAGAAGCG (SEQ ID NO: 74) |

Correlation with Sequence Listing

SEQUENCES OF HUMAN GENES SELECTED PRIMERS USED TO DETECT OXIDATIVE STRESS.

| GENES | ACCESS N° | PRIMER 1 | PRIMER 2 |
|---|---|---|---|
| Anti-oxydant enzymes: | | | |
| Catalase | XM_006202 | Seq01 | Seq02 |
| Mn superoxide dismutase | X14322 | Seq03 | Seq04 |
| Cu/Zn superoxide dismutase | X81859 | Seq05 | Seq06 |
| Thioredoxin 1 | XM_015718 | Seq07 | Seq08 |
| Thioredoxin reductase-1 | XM_015673 | Seq09 | Seq10 |
| Peroxiredoxin-1 | XM_011983 | Seq11 | Seq12 |
| L-ferritin | XM_016853 | Seq13 | Seq14 |
| H-ferritin | XM_017556 | Seq15 | Seq16 |
| Transferrin receptor | XM_002788 | Seq17 | Seq18 |
| Pro-oxydant enzymes: | | | |
| Cyclo-oxygenase-2 | M90100 | Seq19 | Seq20 |
| 5-lipoxygenase | XM_005818 | Seq21 | Seq22 |
| Phospholipase A2 | XM_007544 | Seq23 | Seq24 |
| Phospholipase A alpha | D16234 | Seq25 | Seq26 |
| Phospholipase D1 | NM_002662 | Seq27 | Seq28 |
| Myeloperoxidase | XM_008160 | Seq29 | Seq30 |
| Nitric oxide synthase-2A | XM_008631 | Seq31 | Seq32 |
| Enzymes for the DNA repair: | | | |
| 8-oxoguanine DNA glycosylase | BC000657 | Seq33 | Seq34 |
| Enzymes for glutathione metabolism: | | | |
| Glutathione peroxidase | X58295 | Seq35 | Seq36 |
| Non-Se glutathione phospholipid hydroperoxide | AF090194 | Seq37 | Seq38 |
| γ-glutamylcysteine synthetase | NM_001498 | Seq39 | Seq40 |
| Glucose-6-P dehydrogenase | XM_013149 | Seq41 | Seq42 |
| Stress proteins: | | | |
| Heat shock protein-70 | M11717 | Seq43 | Seq44 |
| Heat shock protein 70 | M15432 | Seq45 | Seq46 |
| Heme oxygenase-1 | XM_009946 | Seq47 | Seq48 |
| Transcription factors: | | | |
| IκB-α | M69043 | Seq49 | Seq50 |
| c-Fos | V01512 | Seq51 | Seq52 |
| Cytokines: | | | |
| Interleukin-8 | AF385628 | Seq53 | Seq54 |
| Interleukin-6 | BC015511 | Seq55 | Seq56 |
| Interleukin-1 | BC008678 | Seq57 | Seq58 |
| House keeping genes: | | | |
| Cyclophilin | | Seq59 | Seq60 |
| β-actin | | Seq61 | Seq62 |
| GAPDH | | Seq63 | Seq64 |

Correlation with Sequence Listing

SEQUENCES OF HUMAN GENES SELECTED LONG OLIGOS USED TO DETECT OXIDATIVE STRESS.

| GENES | ACCESS N° | LONG OLIGO |
|---|---|---|
| Anti-oxydant enzymes: | | |
| Catalase | XM_006202 | Seq65 |
| Mn superoxide dismutase | X14322 | Seq66 |
| Thioredoxin 1 | XM_015718 | Seq67 |
| Thioredoxin reductase-1 | XM_015673 | Seq68 |
| Peroxiredoxin-1 | XM_011983 | Seq69 |
| Enzymes for glutathione metabolism: | | |
| Glutathione peroxidase | X58295 | Seq70 |
| Non-Se glutathione phospholipid hydroperoxide | AF090194 | Seq71 |
| γ-glutamylcysteine synthetase | NM_001498 | Seq72 |
| Glucose-6-P dehydrogenase | XM_013149 | Seq73 |
| Stress proteins: | | |
| Heme oxygenase-1 | XM_009946 | Seq74 |

Results

A. Determination of Reference Blood Concentration of Markers Related to Oxidative Stress.

All of the antioxidants studied showed a normal distribution. Table III lists the reference values for all antioxidants. The mean concentration for vitamin C was significantly higher in women than in men (9.32±4.2 vs. 6.94±3.75 µg/ml; p<0.0001), but the reverse was true for SOD (710.5±94.5 IU/g Hb in men vs. 666.8±72.5 IU/g Hb in women; p<0,05) and uric acid (334.37±73.78 in men vs. 265.72±89.83 µmol/L in women). No significant difference between the sexes was observed for any of the other parameters (not shown).

FIG. 1 shows a slightly dissymmetric distribution for antibodies against oxidized LDL. The calculated mean concentration±SD was 424.19±231.26 mIU/ml. Men and women showed no significant difference for this parameter. Values above 650 mIU/ml were recorded in 19.5% of the subjects (highest value: 1580 mIU/ml). For homocysteine, the distribution was also slightly dissymmetric in the low values. The mean±SD was 11.71±3.58 µmol/L. Women showed a significantly higher homocysteine concentration than men (12.92±4.91 vs. 10.60±3.68 µmol/L, p<0.05). Most of our subjects had values near the mean, but 19.5% of them had levels between 15 and 30 µmol/L. Only one subject had a level above 30 µmol/L.

Regression analysis revealed a weak but significant negative correlation between age on the one hand, and vitamins C ($r^2=0.042$; p=0.021) and E ($r^2=0.063$; p=0.005) on the other. It showed a positive correlation between age and cholesterol ($r^2=0.10$; p=0.0003). Age did not affect the level of homocysteine or of antibodies against oxidized LDL (data not shown). Furthermore, no correlation was observed between either of these risk factors for cardiovascular disease and any antioxidant level, the cholesterol level, or the LDL-cholesterol level.

Table IV shows the influence of smoking (25% of the subjects smoked between 5 and 20 cigarettes a day) on all of the parameters examined in this study. In smokers, the mean vitamin C level was 31% lower than in non-smokers. The selenium and GPx levels were also significantly reduced (by 9% and 13% respectively), but the effect was less pronounced. No significant difference was detected for the other antioxidants. In smokers, the, level of antibodies against oxidized LDL was also lower than in non-smokers, but the difference was not significant. Smokers additionally showed a 13.5% higher tHcy level than non-smokers, this difference appearing almost significant (p=0.066).

The subjects answered a questionnaire regarding fruit consumption (see distribution in Table V) and antioxidant intake. Table V shows that subjects eating between 1 and 4 fruits a day had a 56.9% higher vitamin C level (significant: p<0.0002) than subjects eating no fruit, and a 33.9% higher level than subjects eating 3 to 4 fruits a week (significant: p<0.05). Of the other biochemical parameters, only PSH, selenium, and GPx levels were also higher in subjects eating fruit in large amounts. On the other hand, regular fruit consumption correlated with a significantly reduced tHcy level. Less than 5% of the subjects declared having taken vitamin complexes in the week prior to blood sampling. The essential effect was a vitamin C level 29% above the mean shown in Table I.

B. Detection of Oxidative Stress in 4 Conditions.

Parameters described in "material and methods" section were assessed in four categories of people at risk of developing an oxidative stress: patients hospitalized for cardiac surgery with coronary bypass procedure (n=41), patients undergoing 3 times a week a renal dialysis (n=10), athletes regularly racing half-marathon (n=6), and top soccer players (n=13) belonging to the French national team. Blood samples were collected when all participants were at basal conditions and treated according to procedures assuming the quality as best as possible of parameters analysis. All data were compared to those obtained in a control group of 123 healthy and sedentary volunteers. Underlined numbers represent abnormal mean values of the studied assay that are lower or higher to the corresponding value observed in the control group. Bold values are within the normal range. However, individual analysis of data revealed the presence of a large number of abnormal values as reflected by the subsequent standard deviation (SD).

Table III shows that the oxidative stress was differently evidenced with respect to the investigated group.

In cardiac patients, low values in vitamin C and in SOD were detected. In contrast, the vitE/cholesterol ratio and GPx levels were surexpressed. In a less extent, an increase in antibodies against oxidized LDL and homocysteine was also observed.

Dialysis patients are characterized by reduced concentrations in vitamin C, GPx, SOD, selenium while elevated levels in lipid peroxides, oxidized LDL and homocysteine were evidenced.

People racing half marathons had elevated levels in vitamin C and in Cu/Zn ratio but low concentrations in VitE/cholesterol ratio, GPx and seric iron Top soccer players have the worst profile as evidenced by the large number of abnormal parameters: decrease in vitamin E, vitE/cholesterol ratio, GSH, GSH/GSSG ratio, zinc and increase in GPx, GSSG, Cu/Zn ratio, antibodies against oxidized LDL and oxidized proteins.

TABLE III

OXIDATIVE STRESS IN 4 SELECTED POPULATIONS

|  | Reference values | Cardiac patients | Dialysis | Half marathon | Top soccer players |
|---|---|---|---|---|---|
| ANTIOXIDANTS |  |  |  |  |  |
|  | n = 123 | n = 41 | n = 10 | n = 6 | n = 13 |
| vitamin C (µg/mL) | 4-10 | 5.13 +/- 3.59 | 5.46 +/- 2.46 | 12.46 +/- 2.67 | 9.72 +/- 3.15 |
| vitamin E (µg/mL) | 8-15 | 15.98 +/- 5.44 | 14.99 +/- 5.67 | 9.40 +/- 1.90 | 8.92 +/- 1.74 |
| vitamin E/cholest (mg/g) | 4.40-7 | 8.11 +/- 1.66 | 7.77 +/- 2.47 | 5.16 +/- 0.90 | 4.91 +/- 0.83 |
| GPx (IU/g Hb) | 30-55 | 69.03 +/- 17.14 | 48.7 +/- 18.15 | 34.86 +/- 2.79 | 50.15 +/- 16.90 |
| SOD (IU/g Hb) | 785-1570 | 697.46 +/- 77.53 | 507.4 +/- 169.83 | 939.43 +/- 87.24 | 969.79 +/- 279.69 |

TABLE III-continued

OXIDATIVE STRESS IN 4 SELECTED POPULATIONS

| | Reference values | Cardiac patients | Dialysis | Half marathon | Top soccer players |
|---|---|---|---|---|---|
| reduced glutathione (GSH) (µM) | 753-958 | ND | 814.49 +/− 236.62 | 835.25 +/− 142.63 | <u>717.35 +/− 84.55</u> |
| oxidized glutathione (GSSG) (µM) | 1.17-5.32 | ND | 0.61 +/− 0.86 | 0.721 +/− 0.57 | <u>24.96 +/− 50.62</u> |
| ratio GSH/GSSG | 156-705 | ND | 4199 +/− 3603 | 2282 +/− 2575 | <u>205.79 +/− 218.49</u> |
| SH-proteins (µmol/L) | 216-556 | 349.85 +/− 68.39 | 300.58 +/− 18.60 | ND | 474.10 +/− 94.31 |
| TRACE ELEMENTS | | | | | |
| copper (g/L) | 0.70-1.40 | ND | ND | 1.05 +/− 0.34 | 0.96 +/− 0.12 |
| zinc (g/L) | 0.70-1.20 | ND | ND | 0.76 +/− 0.097 | 0.74 +/− 0.14 |
| ratio Cu/Zn | 1.00-1.17 | ND | ND | 1.41 +/− 0.54 | 1.34 +/− 0.35 |
| selenium (µg/100 ml) | 94-130 | 96.03 +/− 16.73 | <u>71.79 +/− 10.88</u> | 112.71 +/− 13.97 | 107.54 +/− 11.92 |
| MARKERS OF OXIDATIVE DAMAGE | | | | | |
| lipid peroxides (µmol/L) | 48-306 | ND | <u>364.20 +/− 232.46</u> | 195.14 +/− 231.20 | 132.95 +/− 55.09 |
| oxidized LDL (U/L) | 26-117 | ND | <u>159.65 +/− 75.49</u> | 39.54 +/− 4.40 | 48.29 +/− 45.78 |
| antibodies against ox-LDL (U/L) | 200-600 | 415.32 +/− 341.81 | 148.15 +/− 210.70 | 210.38 +/− 38.47 | <u>610.57 +/− 449.83</u> |
| oxidized proteins (nmol/mg prot) | 0.224 +/− 0.209 | ND | 0.207 +/− 0.146 | ND | <u>0.699 +/− 0.366</u> |
| IRON METABOLISM | | | | | |
| seric iron (µmol/L) | 9-33 | ND | ND | <u>2.28 +/− 0.75</u> | 19.89 +/− 6.57 |
| ferritin (ng/mL) | 30-300 | ND | | 195.57 +/− 263.93 | 95.63 +/− 44.59 |
| transferrin (g/L) | 1.60-3.50 | ND | | 2.53 +/− 0.26 | 2.33 +/− 0.26 |
| iron capacity of saturation of transferrin (%) | 20-40 | ND | | 37 +/− 17 | 34 +/− 13 |
| MISCELLANEOUS | | | | | |
| Homocysteine (µmol/L) | 5-15 | 15.36 +/− 3.90 | <u>34.01 +/− 17.04</u> | ND | 8.91 +/− 2.47 |

Underlined numbers represent abnormal mean values of the studied assay that are lower or higher to the corresponding value observed in the control group. Numbers in bold print are within the normal range. However, individual analysis of data revealed the presence of a large number of abnormal values reflected by the subsequent standard deviation (SD).

TABLE IV

COMPARISON OF OXIDATIVE STRESS BETWEEN SMOKERS AND NO SMOKERS.

| | no smokers (n = 92) | Smokers (n = 31) | statistics |
|---|---|---|---|
| vitamin C (µg/ml) | 7.96 ± 3.83 | 5.5 ± 3.37 | $p < 0.005$ |
| vitamin A (µg/100 ml) | 69.94 ± 18.11 | 75.95 ± 21.41 | n.s |
| vitamin E (µg/ml) | 13.98 ± 3.48 | 13.74 ± 3.48 | n.s |
| Cholesterol (mg/l) | 2.01 ± 0.36 | 2.01 ± 0.33 | n.s |
| vitE/cholesterol (mg/g) | 7.01 ± 1.44 | 6.86 ± 1.33 | n.s |
| selenium (µg/l) | 78.56 ± 13.28 | 72.22 ± 13.63 | $p < 0.05$ |
| PSH (µM) | 424.91 ± 137.38 | 413.22 ± 152.62 | n.s |
| SOD (Ul/g Hb) | 699.08 ± 90.25 | 706.71 ± 98.08 | n.s |
| GPx (Ul/g Hb) | 69.77 ± 21.82 | 60.83 ± 18.14 | $p < 0.05$ |
| uric acid (mg/l) | 54.10 ± 14.60 | 55.13 ± 13.30 | n.s |
| oxidized LDL antibodies (mUl/ml) | 493.55 ± 323.67 | 393.25 ± 295.33 | n.s |
| Homocysteine (µM) | 11.96 ± 4.21 | 13.58 ± 5.11 | $p = 0\ldots066$ |

TABLE V

INFLUENCE OF FRUITS INTAKE ON OXIDATIVE STRESS STATUS.

|  | no fruit (n = 33) | 3-4 fruits/week (n = 20) | 1-4 fruits/day (n = 70) |
|---|---|---|---|
| vitamin C (μg/ml) | 5.48 ± 2.62 | 6.42 ± 3.31 | 8.60 ± 4.17*,** |
| vitamin A (μg/100 ml) | 72.82 ± 22.17 | 73.25 ± 15.42 | 70.32 ± 18.68 |
| vitamin E (μg/ml) | 14.16 ± 3.84 | 13.06 ± 2.14 | 14.00 ± 3.48 |
| Cholesterol (mg/l) | 2.04 ± 0.38 | 2.02 ± 0.34 | 2.00 ± 0.34 |
| vitE/cholesterol (mg/g) | 6.94 ± 1.25 | 6.56 ± 1.19 | 7.04 ± 1.53 |
| selenium (μg/l) | 73.39 ± 15.21 | 78.68 ± 14.60 | 77.35 ± 12.20* |
| PSH (μM) | 370.02 ± 77.85 | 413.22 ± 152.62 | 444.26 ± 161.08* |
| SOD (Ul/g Hb) | 717.21 ± 93.11 | 681.74 ± 81.53 | 699.07 ± 93.21 |
| GPx (Ul/g Hb) | 63.09 ± 15.06 | 74.16 ± 36.92 | 68.89 ± 16.56* |
| uric acid (mg/l) | 57.64 ± 16.36 | 54.32 ± 11.49 | 53.19 ± 13.59 |
| oxidized LDL antibodies (mUl/ml) | 447.53 ± 298.19 | 499.36 ± 440.80 | 475.64 ± 295.91 |
| Homocysteine (μM) | 14.75 ± 4.64 | 10.96 ± 3.76* | 11.60 ± 4.14** |

Vitamin C: *$p < 0.0002$ vs. no fruit; **$p < 0.05$ vs. 3-4 fruits a week.
Selenium: *$p < 0.05$ vs. no fruit;
GPx: *$p < 0.05$ vs. no fruit;
PSH: *$p < 0.05$ vs. no fruit
Homocysteine: *$p < 0.05$ vs. no fruit; **$p < 0.005$ vs. no fruit
Hb = hemoglobin C. Microarray Experimentation.

Hybridization signals from the housekeeping control genes should theoretically be the same. Experimentations revealed that it is not exactly the case. The ratio varied from 0.3 to 2.1. As proposed by Wong K K et al. (Biotechniques, 2001, 30: 670-675), such a problem can be overwhelmed by using an average ratio of the three housekeeping genes closed to 1. Thus, the result of internal control for normalizing signal was similar to that of genes that express at a relatively constant level in different conditions.

A. Patient with Chronic Renal Failure (Before Hemodialysis).

When compared to the control population, patient regularly submitted to renal dialysis showed an increasing mRNA expression of catalase (CAT), glucose-6-phosphate deshydrogenase (G6PDH), heat shock protein-70 (HSP 70) and 5-lipoxygenase (5-LPO) (cf. Table VI).

B. Patient Submitted to Cardiac Surgery Associated with Cardio-pulmonary Bypass Procedure.

When compared to basal condition, a down-regulation of 5 genes was observed in lymphocytes isolated 24 h after the surgery. They include superoxide dismutase (Mn-SOD), c-phospholipase A2, H-ferritine, Interleukin-8 (IL-8) and nitric oxide synthase 2 (NOS2).

Among these genes, IL-8 was particularly repressed. In contrast, level of catalase mRNA expression was up-regulated (cf Table VI).

C. Effect of a Half-marathon on Genes Expression.

Figure 2:
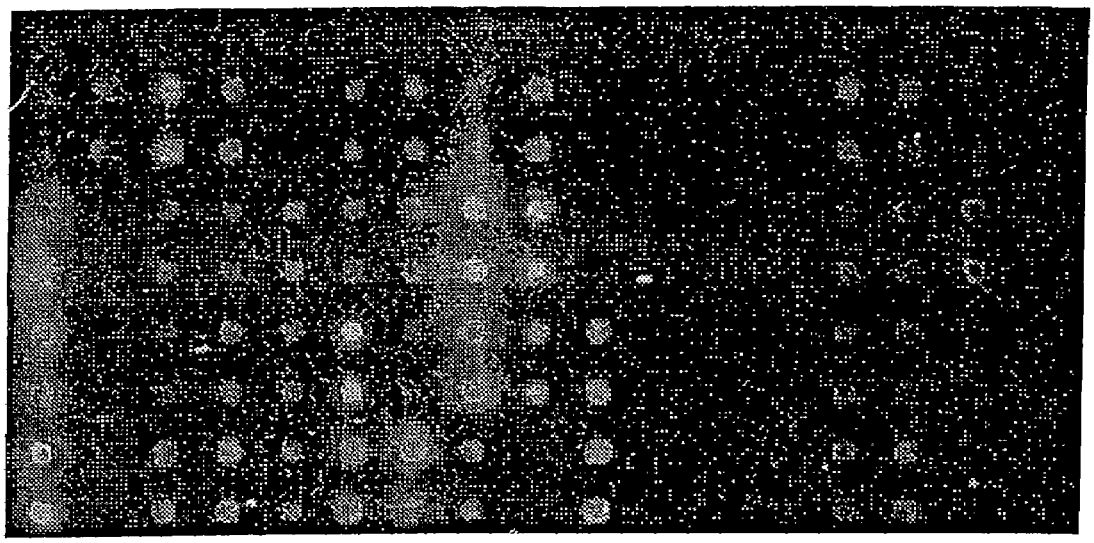
FIG. 2 shows the parallel determination of oxidative stress markers using a microarray assay.

Physical exercise can elevate core temperature to 44° C. and muscle temperatures up to 45° C. Protection and/or tolerance against exercise-induced oxidative, heat, cytokine, and inflammatory stress in leukocytes may be in part provided by heat shock proteins (HSPs) family (Fehrenbach E. and Niess A M. Exerc. Immunol. Rev. 5: 57-77; 1999). Using our microarray assay, we have shown a strong upregulation of HSP70 (cf. Table VI and FIG. 2). In contrast, a large number of genes are down-regulated, and more particularly IκB-α.

TABLE VI

EXPRESSION OF HUMAN GENES CODING FOR PRO AND ANTIOXIDATIVE PROTEINS MODULATED IN DIFFERENT IN VIVO STRESS SITUATION.

| GENES |  | Hemodialysis | Cardiac surgery | Half-marathon |
|---|---|---|---|---|
| Catalase | A1 | 5.889 | 2.054 | 1.144 |
| Peroxyredoxin-1 | A2 | 18.5 | 1.809 | 0.304 |
| Thioredoxine reductase-1 | A3 | 11.144 | 1.4 | 0.356 |
| Mn SOD | B1 | 1.13 | <u>0.277</u> | 0.88 |
| Glucose-6-P deshydrogenase | B2 | 3.613 | 1.26 | 0.746 |
| Thioredoxin-1 | B3 | 1.935 | 0.926 | 1.331 |
| Gluthatione peroxidase | C1 | 3.975 | 0.439 | 1.669 |
| Non-Se glutathione phospholipid hydroperoxide | C2 | 5.215 | 0.825 | <u>0.295</u> |
| γ- glutamylcysteine synthetase | C3 | 2.931 | 1.055 | <u>0.227</u> |
| Cu/Zn SOD | D1 | 6.546 | 0.724 | 0.285 |
| Heme oxygenase-1 | D2 | 4.91 | 0.891 | <u>0.441</u> |
| Heat shock protein-70 | A2 | 5.727 | 1.219 | 14.227 |

TABLE VI-continued

EXPRESSION OF HUMAN GENES CODING FOR PRO AND ANTIOXIDATIVE PROTEINS MODULATED IN DIFFERENT IN VIVO STRESS SITUATION.

| GENES | | Hemodialysis | Cardiac surgery | Half-marathon |
|---|---|---|---|---|
| IκB-α | A3 | 1.924 | 0.551 | 0.292 |
| Cyclo-oxygenase-2 | A4 | 146.667 | 0.834 | 0.342 |
| Phospholipase D-1 | A6 | 7.836 | 0.783 | 0.499 |
| c-Fos | B1 | 7.885 | 1.949 | 1.575 |
| Transferrin receptor | B3 | 11.367 | 2.183 | 0.587 |
| 5-lipoxygenase | B4 | 8.613 | 1.766 | 0.814 |
| c-phospholipase A2 | B5 | 1.155 | 0.247 | 0.442 |
| Myeloperoxidase | B6 | 1.038 | 0.51 | 0.794 |
| L-ferritine | C1 | 1.332 | 0.789 | 0.929 |
| H-ferritine | C2 | 0.397 | 0.21 | 0.455 |
| IL-8 | C3 | 1.411 | 0.058 | 0.272 |
| IL-6 | C4 | | | 0.998 |
| Human 8-oxoguanine DNA glycosylase | C6 | 0.839 | 0.593 | 0.336 |
| IL-1 | D1 | 1.839 | 0.528 | 0.454 |
| Phospholipase A alpha | D2 | 3.593 | 0.584 | 0.187 |
| Heat shock protein 70 | D3 | 4.818 | 1.118 | 25.662 |
| Nitric oxide synthase-2 | D4 | 0.737 | 0.446 | 0.229 |
| House keeping genes mean | | 1.336 | 0.874 | 1.060 |

The background-substracted intensities of all cDNA and oligo hybridizations were normalized to each other by the ratios of total Cy3 and Cy5-fluorescence values (only values in fluorescence intensity greater than 1000 are significant). Three housekeeping genes (cyclophilin, β-actin and GAPDH) have been used as internal controls. The Cy3-to-Cy5 ratios for each of these control genes must be closed to 1. Underlined numbers represent a down-regulation of the mRNA. Numbers in bold print represent an up-regulation of the mRNA.

The invention claimed is:

1. A method for determining the relative amounts of oxidative stress markers in a group of individuals determined to have a risk factor for oxidative stress, which method comprises:
   (i) measuring the amount of at least 10 different oxidative stress markers in a sample of whole blood or component thereof obtained from each individual of the group of individuals determined to have a risk factor for oxidative stress; and
   (ii) comparing the amount of each of the oxidative stress markers in the group of individuals determined to have a risk factor for oxidative stress with the amount of each of the oxidative stress markers measured in a group of healthy individuals;
   whereupon the relative amounts of oxidative stress markers in the group of individuals determined to have a risk factor for oxidative stress relative to healthy individuals are determined.

2. A method for the detection of oxidative stress in an individual having a risk factor for oxidative stress, which method comprises:
   (i) selecting at least two oxidative stress markers, which have been determined in accordance with the method of claim 1 to increase or decrease in individuals with that risk factor relative to healthy individuals;
   (ii) measuring the amounts of the at least two oxidative stress markers in a sample of whole blood or component thereof obtained from the individual; and
   (iii) comparing the amounts of the at least two oxidative stress markers in the sample obtained from the individual with the amounts of the same at least two oxidative stress markers in healthy individuals;
   whereupon the individual is determined to have oxidative stress or not.

3. The method of claim 2, which comprises, in (i), selecting not more than 22 oxidative stress markers that increase or decrease in individuals with that risk factor relative to healthy individuals.

4. The method according to claim 1, wherein the risk factor is selected from: unbalanced diet, smoking habits, exposure to toxic environment, medical surgery, intense physical exercise, and diseases affecting the kidneys, lungs, heart, skin, brain, joints, gastrointestinal tract, eyes, blood vessels, red blood cells, liver and multiple organs.

5. The method according to claim 4, wherein the diseases are selected from transplantation, glomerular nephritis, respiratory distress syndrome, asthma, coronary thrombosis, bums, sunlight exposure, psoriasis, dermatosis, trauma, Parkinson's disease, neurotoxins, dementia, rheumatoid arthritis, diabetes, pancreatitis, endotoxemia, intestinal Ischaemia, cataract, retinopathy, retinal degeneration, atherosclerosis, Fanconi's anemia, malaria, inflammation, ischaemia-reperfusion, drug toxicity, iron overload, nutritional deficiency, alcohol, radiation, cancer, aging, HCV infection and AIDS.

6. The method according to claim 1, wherein the oxidative stress marker is selected from the group consisting of: antioxidants, trace elements, indicators of oxidative stress, iron metabolism markers, homocysteine, enzymes having antioxidant functions, enzymes having pro-oxidant functions, enzymes for DNA repair, enzymes of the glutathione metabolism, stress proteins, proteins implied in apoptosis, transcription factors, cytokines and chemokines.

7. The method according to claim 6, wherein the antioxidant is selected from: vitamin A, vitamin C, vitamin E, reduced glutathione (GSH)/oxidized glutathione (GSSG), protein thiols, glutathione peroxidase and superoxide dismutase.

8. The method according to claim 6, wherein the trace element is selected from selenium, cooper and zinc.

9. The method of claim 6, wherein the indicator of oxidative stress is selected from 8-hydroxy-2'-deoxyguanosine, myeloperoxidase, glucose, glyoxal, and an antibody against oxidized LDL.

10. The method according to claim 6, wherein the iron metabolism marker is selected from transferrin, ferritin and ceruloplasmin.

11. The method according to claim 6, wherein the enzymes having antioxidant function are selected from catalase, Mn-containing superoxide dismutase (SOD), Copper and zinc containing SOD, thioredoxine-1, thioredoxine reductase-1, peroxyredoxine-1, metallothioneine-1, L-ferritine, H-ferritine and transferrine receptor, anti-oxidant protein 2, ceruloplasmin, lactoferrin, selenoprotein P, selenoprotein W, frataxin, serum paraoxonase/arylesterase 1, serum paraoxonase/arylesterase 2, and serum paraoxonase/arylesterase 3.

12. The method according to claim 6, wherein the enzymes having pro-oxidant functions are selected from cyclooxygenase-2,5-lipoxygenase, cphospholipase A2, phospholipase A alpha, phospholipase D-1, myeloperoxidase, nitric oxide synthetase, C reactive protein, elastase, haptoglobin, NADH-cytochrome b5 reductase and diaphorase A1.

13. The method according to claim 6, wherein the enzyme for DNA repair may be selected from is 8-oxoguanine DNA glycosylase.

14. The method according to claim 6, wherein the glutathione metabolism enzyme may is selected from glutathione peroxidase, non-Se glutathione phospholipid hydroperoxide, phospholipid, gamma-glutamyl cysteine synthetase, and glucose 6-phosphate dehydrogenase, extracellular glutathione peroxidase, glutathione peroxidase, glutathione peroxidase 2, glutathione peroxidase 4, glutathione reductase, glutathione S-transferase, glutathione synthetase, peroxiredoxin 1, peroxiredoxin 2, peroxiredoxin 3, peroxiredoxin 5, and thioredoxin 2.

15. The method according to claim 6, wherein the stress protein is a heat shock protein (HSP) in, heme-oxygenase-1, heme-oxygenase-2, 150 kDa oxygen-regulated protein (ORP)150, 27 kDa HSP27, HSP90A, HSP17, HSP40 or HSP 110.

16. The method according to claim 6, wherein the protein implied in apoptosis is FasL, CD95, tumor necrosis factor (TNF) receptor 1, Bcl-2, GADD 153, GADD45, RAD50, RAD51B, RAD52, RAD54, p53 or Fas ligand.

17. The method according to claim 6, wherein the transcription factor is selected from NfkB-a, c-Fos, C-jun, IκB-α, monoamine oxidase A, monoamine oxidase B, and peroxisome proliferative-activated receptor α.

18. The method according to claim 6, wherein the cytokine or chemokine is selected from: IL-1, IL-6, IL-8, IL-1beta, IL-2 and TNF1 receptor associated protein.

19. The method according to claim 1, when the risk factor of said individual is hemodialysis, and the oxidative marker is selected from the group of catalase, glucose 6 phosphate dehydrogenase, HSP70, 5-lipoxygenase, vitamin C, glutathione peroxidase, SOD, Se, lipid peroxide, oxidized LDL and homocysteine.

20. The method according to claim 1, when the risk factor of said individual in cardiac surgery, and the oxidative marker is selected from the group of superoxide dismutase containing manganese, c-phospholipase A2, H-ferritin, IL-8, nitric oxide synthase 2 (NOS2), vitamin C, vitamin E/cholesterol, glutathione peroxidase (GPx), antibodies against LDL and homocysteine.

21. The method according to claim 1, when the risk factor of said individual is intense physical exercise, the oxidative marker is selected from the group of vitamin B, vitamin E/cholesterol, GSH, GSH/GSSG ratio, zinc, GPx, GSSG, copper/zinc ratio, antibodies against oxidized LDL and oxidized proteins.

22. The method according to claim 1, when the risk factor of said individual is exhaustion due to physical exercise and injuries, the oxidative marker is selected from the group of vitamin E, vitamin E/cholesterol, GSH, GSH/GSSG ratio, zinc, GPx, GSSG; copper/zinc ratio, antibodies against oxidized LDL and oxidized proteins.

23. The method according to claim 1, when the risk factor of said individual is smoking, the oxidative marker is selected from the group of vitamin C, Se, GPx, antibodies against oxidized LDL and homocysteine.

24. The method according to claim 1, wherein the amount of the oxidative stress marker is determined by measuring the concentration of the oxidative marker.

25. The method according to claim 1, wherein the amount is determined by measuring the concentration of the gene transcript/mRNA encoding the oxidative marker.

26. The method according to claim 25, wherein the amount of at least two oxidative stress markers is determined in parallel.

27. The method according to claim 26, wherein the amount of oxidative stress marker is measured by using a DNA chip.

28. A process of detecting oxidative stress in a blood sample comprising cells, which method comprises:
   (i) extracting mRNA from cells from the blood sample,
   (ii) reverse transcribing the mRNA into cDNA, with labeling of the cDNA, and
   (iii) contacting the cDNA with a population of synthetic DNA fragments under hybridizing conditions, wherein the population of synthetic DNA fragments hybridizes with the cDNA when present due to gene expression under oxidative stress, and simultaneously detecting hybridization,
   whereupon oxidative stress in a blood sample comprising cells is detected.

29. The process according to claim 28, wherein said blood sample is a preparation of lymphocytes.

30. The process according to claim 28, characterized in that step c. is realized on a DNA chip array, which bears said synthetic DNA fragments according to a specific topography.

31. The process according to claim 28, characterized in that the population of synthetic DNA fragments is composed of oligonucleotides having a size of between 25 to 100 b.

32. The process according to claim 28, characterized in that the population of the synthetic DNA fragments is composed of in vitro polymerase chain reaction (PCR) enzymatic amplification products.

33. The process according to claim 28, characterized in that the population of synthetic DNA fragments is composed of oligonucleotides having a size of between 25 and 100 b, and of products coming from in vitro PCR enzymatic amplification.

34. The process according to claim 28, characterized in that the population of synthetic DNA fragments comprises at least some gene fragments belonging to a family of genes chosen from the group constituted by the one coding for:
   a. enzymes with antioxidant functions, enzymes with pro-oxidant functions, b. enzymes for the DNA repair,
c. enzymes of the glutathion metabolism,
d. stress proteins,
e. proteins implied in apoptosis,
f. transcription factors,
g. cytokines, or
h. chemokines.

35. The process according to claim 34, characterized in that the population of synthetic DNA fragments comprises at least two genes, each of which belongs to one of the families of genes a-h.

36. The process according to claim 28, characterized in that it comprises, in addition, before said mRNA extraction, an in vitro exposition of the cells of the blood sample to factors generating oxidative stress.

37. The process according to claim 28, characterized in that it comprises in parallel a quantification of blood markers of oxidative stress.

38. The method according to claim 3, wherein not more than 15 different oxidative stress markers are selected.

39. The method according to claim 38, wherein not more than 10 different oxidative stress markers are selected.

40. The method according to claim 39, wherein not more than 5 different oxidative stress markers are selected.

41. The method according to claim 2, wherein the amount of he oxidative stress marker is determined by measuring the concentration of the oxidative marker.

* * * * *

SEQUENCE LISTING

<160> NUMBER OF SEQ ID NOS: 76

<210> SEQ ID NO 1
<211> LENGTH: 27
<212> TYPE: DNA
<213> ORGANISM: Homo sapiens

<400> SEQUENCE: 1
gatatggatc acatactttc aagctgg                                        27

<210> SEQ ID NO 2
<211> LENGTH: 25
<212> TYPE: DNA
<213> ORGANISM: Homo sapiens

<400> SEQUENCE: 2
ggtagggaca gttcacaggt atatg                                          25

<210> SEQ ID NO 3
<211> LENGTH: 26
<212> TYPE: DNA
<213> ORGANISM: Homo sapiens

<400> SEQUENCE: 3
gtggtggtca tatcaatcat agcatt                                         26

<210> SEQ ID NO 4
<211> LENGTH: 27
<212> TYPE: DNA
<213> ORGANISM: Homo sapiens

<400> SEQUENCE: 4

```
cattccaaat agcttttaga taatcag                                            27

<210> SEQ ID NO 5
<211> LENGTH: 23
<212> TYPE: DNA
<213> ORGANISM: Homo sapiens

<400> SEQUENCE: 5
gcaatgtgac tgctgacaaa gat                                                23

<210> SEQ ID NO 6
<211> LENGTH: 23
<212> TYPE: DNA
<213> ORGANISM: Homo sapiens

<400> SEQUENCE: 6
atgatgcaat ggtctcctga gag                                                23

<210> SEQ ID NO 7
<211> LENGTH: 23
<212> TYPE: DNA
<213> ORGANISM: Homo sapiens

<400> SEQUENCE: 7
ttgtagtagt tgacttctca gcc                                                23

<210> SEQ ID NO 8
<211> LENGTH: 23
<212> TYPE: DNA
<213> ORGANISM: Homo sapiens

<400> SEQUENCE: 8 ccacctttg tcccttctta aaa                                                 23

<210> SEQ ID NO 9
<211> LENGTH: 28
<212> TYPE: DNA
<213> ORGANISM: Homo sapiens

<400> SEQUENCE: 9
cctatgacta tgaccttatc atcattgg                                           28

<210> SEQ ID NO 10
<211> LENGTH: 25
<212> TYPE: DNA
<213> ORGANISM: Homo sapiens

<400> SEQUENCE: 10
ccttaatcct gtgaggacca ataaa                                              25

<210> SEQ ID NO 11
<211> LENGTH: 26
<212> TYPE: DNA
<213> ORGANISM: Homo sapiens

<400> SEQUENCE: 11
ttctttcaga tttgacccat cagatc                                             26

<210> SEQ ID NO 12
<211> LENGTH: 25
<212> TYPE: DNA
<213> ORGANISM: Homo sapiens
```

```
<400> SEQUENCE: 12
gggattatct gtttcactac caggt                                      25

<210> SEQ ID NO 13
<211> LENGTH: 24
<212> TYPE: DNA
<213> ORGANISM: Homo sapiens

<400> SEQUENCE: 13
ccagattcgt cagaattatt ccac                                       24

<210> SEQ ID NO 14
<211> LENGTH: 23
<212> TYPE: DNA
<213> ORGANISM: Homo sapiens

<400> SEQUENCE: 14
taagcttcac ttcctcatct agg                                        23

<210> SEQ ID NO 15
<211> LENGTH: 25
<212> TYPE: DNA
<213> ORGANISM: Homo sapiens

<400> SEQUENCE: 15
tcttcaccaa tctcatgagg agagg                                      25

<210> SEQ ID NO 16
<211> LENGTH: 24
<212> TYPE: DNA
<213> ORGANISM: Homo sapiens

<400> SEQUENCE: 16
tggtcacatg gtcatccaat tctt                                       24

<210> SEQ ID NO 17
<211> LENGTH: 29
<212> TYPE: DNA
<213> ORGANISM: Homo sapiens

<400> SEQUENCE: 17
tttatacact cctgtgaatg gatctatag                                  29

<210> SEQ ID NO 18
<211> LENGTH: 26
<212> TYPE: DNA
<213> ORGANISM: Homo sapiens

<400> SEQUENCE: 18
caacatagtg atctggttct acaaag                                     26

<210> SEQ ID NO 19
<211> LENGTH: 30
<212> TYPE: DNA
<213> ORGANISM: Homo sapiens

<400> SEQUENCE: 19
cagaaataca actatcaaca gtttatctac                                 30

<210> SEQ ID NO 20
<211> LENGTH: 25
<212> TYPE: DNA
<213> ORGANISM: Homo sapiens
```

-continued

```
<400> SEQUENCE: 20
gtaggcagga gaacatataa catta                                          25

<210> SEQ ID NO 21
<211> LENGTH: 27
<212> TYPE: DNA
<213> ORGANISM: Homo sapiens

<400> SEQUENCE: 21
tgatatccag tttgatagtg aaaaagg                                        27

<210> SEQ ID NO 22
<211> LENGTH: 23
<212> TYPE: DNA
<213> ORGANISM: Homo sapiens

<400> SEQUENCE: 22
gaagggagga aatagggtt ctc                                             23

<210> SEQ ID NO 23
<211> LENGTH: 25
<212> TYPE: DNA
<213> ORGANISM: Homo sapiens

<400> SEQUENCE: 23
ctcatcctgt cattggacta caacc                                          25

<210> SEQ ID NO 24
<211> LENGTH: 24
<212> TYPE: DNA
<213> ORGANISM: Homo sapiens

<400> SEQUENCE: 24
ggttgttgca gacattgtaa tgtg                                           24

<210> SEQ ID NO 25
<211> LENGTH: 29
<212> TYPE: DNA
<213> ORGANISM: Homo sapiens

<400> SEQUENCE: 25
cattagtgat aaagatgcct ctatagtag                                      29

<210> SEQ ID NO 26
<211> LENGTH: 27
<212> TYPE: DNA
<213> ORGANISM: Homo sapiens

<400> SEQUENCE: 26
cacatcatag taagcaataa gtaagtc                                        27

<210> SEQ ID NO 27
<211> LENGTH: 30
<212> TYPE: DNA
<213> ORGANISM: Homo sapiens

<400> SEQUENCE: 27
ctgacatgag taatatcata gaaaatctgg                                     30

<210> SEQ ID NO 28
<211> LENGTH: 29
<212> TYPE: DNA
```

```
<213> ORGANISM: Homo sapiens

<400> SEQUENCE: 28
ccatgtgtta attcaatagt gtaaagatt                                    29

<210> SEQ ID NO 29
<211> LENGTH: 24
<212> TYPE: DNA
<213> ORGANISM: Homo sapiens

<400> SEQUENCE: 29
gttcctacaa tgactcagtg gacc                                         24

<210> SEQ ID NO 30
<211> LENGTH: 23
<212> TYPE: DNA
<213> ORGANISM: Homo sapiens

<400> SEQUENCE: 30
catactgctc catcagtttc ctc                                          23

<210> SEQ ID NO 31
<211> LENGTH: 28
<212> TYPE: DNA
<213> ORGANISM: Homo sapiens

<400> SEQUENCE: 31
cttcatgaag tacatgcaga atgaatac                                     28

<210> SEQ ID NO 32
<211> LENGTH: 24
<212> TYPE: DNA
<213> ORGANISM: Homo sapiens

<400> SEQUENCE: 32
cctgtactta tccatgcaga caac                                         24

<210> SEQ ID NO 33
<211> LENGTH: 25
<212> TYPE: DNA
<213> ORGANISM: Homo sapiens

<400> SEQUENCE: 33
caagtatgga cactgactca gactg                                        25

<210> SEQ ID NO 34
<211> LENGTH: 23
<212> TYPE: DNA
<213> ORGANISM: Homo sapiens

<400> SEQUENCE: 34
atgtgccaca tatggacatc cac                                          23

<210> SEQ ID NO 35
<211> LENGTH: 23
<212> TYPE: DNA
<213> ORGANISM: Homo sapiens

<400> SEQUENCE: 35
gacaagagaa gtcgaagatg gac                                          23

<210> SEQ ID NO 36
<211> LENGTH: 23
```

```
<212> TYPE: DNA
<213> ORGANISM: Homo sapiens

<400> SEQUENCE: 36
tcttcctgta gtgcattcag ttc                                          23

<210> SEQ ID NO 37
<211> LENGTH: 23
<212> TYPE: DNA
<213> ORGANISM: Homo sapiens

<400> SEQUENCE: 37
agactcatgg ggcattctct tct                                          23

<210> SEQ ID NO 38
<211> LENGTH: 24
<212> TYPE: DNA
<213> ORGANISM: Homo sapiens

<400> SEQUENCE: 38
caggaccaaa aataaacacc acac                                         24

<210> SEQ ID NO 39
<211> LENGTH: 30
<212> TYPE: DNA
<213> ORGANISM: Homo sapiens

<400> SEQUENCE: 39
catttataga aacatttact gaggatgatg                                   30

<210> SEQ ID NO 40
<211> LENGTH: 25
<212> TYPE: DNA
<213> ORGANISM: Homo sapiens

<400> SEQUENCE: 40
tgtctattga gtcatatcgg gattt                                        25

<210> SEQ ID NO 41
<211> LENGTH: 24
<212> TYPE: DNA
<213> ORGANISM: Homo sapiens

<400> SEQUENCE: 41
tctatgtgga gaatgagagg tggg                                         24

<210> SEQ ID NO 42
<211> LENGTH: 23
<212> TYPE: DNA
<213> ORGANISM: Homo sapiens

<400> SEQUENCE: 42
ataaatatag gggatgggct tgg                                          23

<210> SEQ ID NO 43
<211> LENGTH: 23
<212> TYPE: DNA
<213> ORGANISM: Homo sapiens

<400> SEQUENCE: 43
ccatggtgct gaccaagatg aag                                          23

<210> SEQ ID NO 44
```

-continued

```
<211> LENGTH: 23
<212> TYPE: DNA
<213> ORGANISM: Homo sapiens

<400> SEQUENCE: 44
gctgatgtcc ttcttgtgtt ttc                                           23

<210> SEQ ID NO 45
<211> LENGTH: 23
<212> TYPE: DNA
<213> ORGANISM: Homo sapiens

<400> SEQUENCE: 45
ccatgacgaa agacaacaat ctg                                           23

<210> SEQ ID NO 46
<211> LENGTH: 23
<212> TYPE: DNA
<213> ORGANISM: Homo sapiens

<400> SEQUENCE: 46
agatgacctc ttgacacttg tcc                                           23

<210> SEQ ID NO 47
<211> LENGTH: 23
<212> TYPE: DNA
<213> ORGANISM: Homo sapiens

<400> SEQUENCE: 47
caggcagagg gtgatagaag agg                                           23

<210> SEQ ID NO 48
<211> LENGTH: 23
<212> TYPE: DNA
<213> ORGANISM: Homo sapiens

<400> SEQUENCE: 48
gagtgtaagg acccatcgga gaa                                           23

<210> SEQ ID NO 49
<211> LENGTH: 24
<212> TYPE: DNA
<213> ORGANISM: Homo sapiens

<400> SEQUENCE: 49
tctacactta gcctctatcc atgg                                          24

<210> SEQ ID NO 50
<211> LENGTH: 23
<212> TYPE: DNA
<213> ORGANISM: Homo sapiens

<400> SEQUENCE: 50
tgaaggtttt ctagtgtcag ctg                                           23

<210> SEQ ID NO 51
<211> LENGTH: 25
<212> TYPE: DNA
<213> ORGANISM: Homo sapiens

<400> SEQUENCE: 51
gagacagacc aactagaaga tgaga                                         25
```

```
<210> SEQ ID NO 52
<211> LENGTH: 23
<212> TYPE: DNA
<213> ORGANISM: Homo sapiens

<400> SEQUENCE: 52
atagaaggac ccagataggt cca                                          23

<210> SEQ ID NO 53
<211> LENGTH: 25
<212> TYPE: DNA
<213> ORGANISM: Homo sapiens

<400> SEQUENCE: 53
ataaagacat actccaaacc tttcc                                        25

<210> SEQ ID NO 54
<211> LENGTH: 23
<212> TYPE: DNA
<213> ORGANISM: Homo sapiens

<400> SEQUENCE: 54
ggtccactct caatcactct cag                                          23

<210> SEQ ID NO 55
<211> LENGTH: 30
<212> TYPE: DNA
<213> ORGANISM: Homo sapiens

<400> SEQUENCE: 55
tttaaatatg tgaagctgag ttaatttatg                                   30

<210> SEQ ID NO 56
<211> LENGTH: 25
<212> TYPE: DNA
<213> ORGANISM: Homo sapiens

<400> SEQUENCE: 56
aatgccattt attggtataa aaacc                                        25

<210> SEQ ID NO 57
<211> LENGTH: 27
<212> TYPE: DNA
<213> ORGANISM: Homo sapiens

<400> SEQUENCE: 57
gagaagaaag taatgacaaa atacctg                                      27

<210> SEQ ID NO 58
<211> LENGTH: 25
<212> TYPE: DNA
<213> ORGANISM: Homo sapiens

<400> SEQUENCE: 58
aaattgcatg gtgaagtcag ttata                                        25

<210> SEQ ID NO 59
<211> LENGTH: 31
<212> TYPE: DNA
<213> ORGANISM: Homo sapiens

<400> SEQUENCE: 59
gtccgggagc catgccgtgt tcttcgacat t                                 31
```

<210> SEQ ID NO 60
<211> LENGTH: 31
<212> TYPE: DNA
<213> ORGANISM: Homo sapiens

<400> SEQUENCE: 60
cgacgcccgc tgatatggcc tccacaatat t                           31

<210> SEQ ID NO 61
<211> LENGTH: 31
<212> TYPE: DNA
<213> ORGANISM: Homo sapiens

<400> SEQUENCE: 61
cgacgcccgc tgatatggcc tccacaatat t                           31

<210> SEQ ID NO 62
<211> LENGTH: 20
<212> TYPE: DNA
<213> ORGANISM: Homo sapiens

<400> SEQUENCE: 62
caccttcacc gttccagttt                                        20

<210> SEQ ID NO 63
<211> LENGTH: 20
<212> TYPE: DNA
<213> ORGANISM: Homo sapiens

<400> SEQUENCE: 63
cgagatccct ccaaaatcaa                                        20

<210> SEQ ID NO 64
<211> LENGTH: 20
<212> TYPE: DNA
<213> ORGANISM: Homo sapiens

<400> SEQUENCE: 64
tgagcttgac aaagtggtcg                                        20

<210> SEQ ID NO 65
<211> LENGTH: 65
<212> TYPE: DNA
<213> ORGANISM: Homo sapiens

<400> SEQUENCE: 65
gagcctggat gtggctcccg tagtcagggt ggacctcagt gaagttcttg accgctttct   60
tctgg                                                             65

<210> SEQ ID NO 66
<211> LENGTH: 65
<212> TYPE: DNA
<213> ORGANISM: Homo sapiens

<400> SEQUENCE: 66
gctgtaacat ctccctttgc caacgcctcc tggtacttct cctcggtgac gttcaggttg   60
ttcac                                                             65

<210> SEQ ID NO 67
<211> LENGTH: 62
<212> TYPE: DNA
<213> ORGANISM: Homo sapiens

```
<400> SEQUENCE: 67
ggcccacacc acgtggctga aagtcaact actacaagtt tatcacctgc agcgtccaag    60
gc                                                                  62

<210> SEQ ID NO 68
<211> LENGTH: 65
<212> TYPE: DNA
<213> ORGANISM: Homo sapiens

<400> SEQUENCE: 68
ccagcaagaa atccagcgca ctccaaagcg acataggatg ctccaacaac cagggtctta    60
cccgg                                                               65

<210> SEQ ID NO 69
<211> LENGTH: 63
<212> TYPE: DNA
<213> ORGANISM: Homo sapiens

<400> SEQUENCE: 69
agctgttcct tcccagtagg gcgctggctt ggaaatcttc gctttgctta ggtgcaggga    60
gtg                                                                 63

<210> SEQ ID NO 70
<211> LENGTH: 65
<212> TYPE: DNA
<213> ORGANISM: Homo sapiens

<400> SEQUENCE: 70
caaagttcca gcggatgtcg tgaaccttca tgggttccca gaagaggcgg tcagatgtac    60
ccagg                                                               65

<210> SEQ ID NO 71
<211> LENGTH: 65
<212> TYPE: DNA
<213> ORGANISM: Homo sapiens

<400> SEQUENCE: 71
ggctggggtg tgtagcggag gtatttcttg ccagatggga gctctttggt gaagactcct    60
ttagg                                                               65

<210> SEQ ID NO 72
<211> LENGTH: 65
<212> TYPE: DNA
<213> ORGANISM: Homo sapiens

<400> SEQUENCE: 72
ccttccggcg ttttcgcatg ttggcctcaa ctgtattgaa ctcggacatt gttcctccgt    60
agggc                                                               65

<210> SEQ ID NO 73
<211> LENGTH: 65
<212> TYPE: DNA
<213> ORGANISM: Homo sapiens

<400> SEQUENCE: 73
aggatgaagg gcaccccatc ccacctctca ttctccacat agaggacgac ggctgcaaaa    60
gtggc                                                               65
```

```
<210> SEQ ID NO 74
<211> LENGTH: 65
<212> TYPE: DNA
<213> ORGANISM: Homo sapiens

<400> SEQUENCE: 74
ggcataaagc cctacagcaa ctgtcgccac cagaaagctg agtgtaagga cccatcggag    60
aagcg                                                               65

<210> SEQ ID NO 75
<211> LENGTH: 14
<212> TYPE: DNA
<213> ORGANISM: Homo sapiens

<400> SEQUENCE: 75
gtccgggagc catg                                                     14

<210> SEQ ID NO 76
<211> LENGTH: 15
<212> TYPE: DNA
<213> ORGANISM: Homo sapiens

<400> SEQUENCE: 76
cgacgcccgc tgata                                                    15
```